US008658407B2

(12) United States Patent
Lyons et al.

(10) Patent No.: US 8,658,407 B2
(45) Date of Patent: Feb. 25, 2014

(54) COMPOSITIONS AND METHODS FOR CONVERSION OF LIGNOCELLULOSIC MATERIAL TO FERMENTABLE SUGARS AND PRODUCTS PRODUCED THEREFROM

(75) Inventors: Mark P. Lyons, Lexington, KY (US); Brian J. Hoskins, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 554 days.

(21) Appl. No.: 12/726,248

(22) Filed: Mar. 17, 2010

(65) Prior Publication Data

US 2010/0248320 A1    Sep. 30, 2010

Related U.S. Application Data

(60) Provisional application No. 61/160,969, filed on Mar. 17, 2009.

(51) Int. Cl.
*C12P 7/10*    (2006.01)
(52) U.S. Cl.
USPC ........................... 435/165; 435/161; 435/163
(58) Field of Classification Search
None
See application file for complete search history.

(56) References Cited

U.S. PATENT DOCUMENTS

| 5,231,017 A | 7/1993 | Lantero et al. |
| 2003/0170834 A1 | 9/2003 | Gatenby et al. |

FOREIGN PATENT DOCUMENTS

| WO | 2004/103086 | 12/2004 |

OTHER PUBLICATIONS

Lin and Tanaka, Ethanol fermentation from biomass resources: current state and prospects, App. Microbiol. Biotechnol. 2006, 69(6):627-642.
Belyea et al., Composition of corn and distillers dried grains with solubles from dry grind ethanol processing, Bioresour Technol. Sep. 2004;94(3):293-8.
Chandra et al., Substrate pretreatment: the key to effective enzymatic hydrolysis of lignocellulosics?, Adv Biochem Eng Biotechnol. 2007;108:67-93.
de Cruz et al., Structural Complexity of the Nitrogen Source and Influence on Yeast Growth and Fermentation, 2002, J Instit. Brewing, 108, 54-61.
Galbe et al., Pretreatment of lignocellulosic materials for efficient bioethanol production, Adv Biochem Eng Biotechnol. 2007;108:41-65.
Graves, Yeast and corn mash fermentation, Ph.D. Thesis, Heriot-Watt University, Scotland, 2007.
Hahn-Hagerdal et al., Bio-ethanol—the fuel of tomorrow from the residues of today, Trends Biotechnol. Dec. 2006;24 (12):549-56. Epub Oct. 16, 2000.
Ham et al., Wet corn distillers byproducts compared with dried corn distillers grains with solubles as a source of protein and energy for ruminants, J Anim Sci. Dec. 1994;72(12):3246-57.
Jones et al., Fuel alcohol production: appraisal of nitrogenous yeast foods for very high gravity wheat mash fermentation, Process Biochemistry, vol. 29, Issue 6, 1994, pp. 483-488.
Krishna, Solid-state fermentation systems-an overview, Crit Rev Biotechnol. Jan.-Jun. 2005;25(1-2):1-30.
Lonsane et al (1992) Exoenzymes, In: Solid Substrate Cultivation, Mitchell et al., Eds., Elsevier Applied Science, London, pp. 191-209.
Mitchell (1992) Microbial basis of process, In: Solid Substrate Cultivation, Rolz, Ed., Elsevier Applied Science, London, UK, pp. 17-28.
Mitchell et al (1992) Definition, characteristics, and potential, In: Solid Substrate Cultivation, Rolz, Ed., Elsevier Applied Science, London, UK, pp. 1-16.
Mitchell et al (2006) Solid-state fermentation bioreactors: Fundamentals of design and operation, Springer, Berlin, Germany.
Mudgett (1986) Solid-state fermentations, In: Manual of Industrial Microbiology and Biotechnology, Demain et al., Eds., American Society for Microbiology, Washington, DC, pp. 66-83.
Padmaja et al. (1999) Oriental fermented foods, In: Biotechnology: Food Fermentation, Microbiology, Biochemistry and Technology, Joshi et al., Eds., Educational Publishers and Distributers, New Delhi, India, pp. 523-582.
Pandey et al. (2001) Solid-state fermentation in biotechnology: Fundamentals and applications, Asiatech Publishers, New Delhi, India, pp. vii-ix and 217-221.
Pérez-Carrillo et al, Effect of Protease Treatment Before Hydrolysis with α-Amylase on the Rate of Starch and Protein Hydrolysis of Maize, Whole Sorghum, and Decorticated Sorghum, Cereal Chemistry Journal, Nov./Dec. 2007, vol. 84, No. 6 , pp. 607-613.
Sánchez et al., Trends in biotechnological production of fuel ethanol from different feedstocks, Bioresour Technol. Sep. 2008;99(13):5270-95. Epub Dec. 26, 2007.
Singh et al., Comparison of Modified Dry-Grind Corn Processes for Fermentation Characteristics and DDGS Composition, Cereal Chemistry Journal, Mar./Apr. 2005, vol. 82, No. 2 , pp. 187-190.
Sun et al., Hydrolysis of lignocellulosic materials for ethanol production: a review, Bioresour Technol. May 2002;83 (1):1-11.
Villas-Bôas et al., Microbial conversion of lignocellulosic residues for production of animal feeds, Animal Feed Science and Technology, vol. 98, Issues 1-2,1 Jul. 2002, pp. 1-12.
Belewu, M. A., & Babalola, F. T. (2009). Nutrient enrichment of waste agricultural residues after solid state fermentation using *Rhizopus oligosporus*. Journal of Applied Biosciences, 13, 695-699.
Shrestha, Prachand. Enhanced bioprocessing of lignocellulose: Wood-rot fungal saccharification and fermentation of corn fiber to ethanol. ProQuest, 2008.
Brown, R. C. (2005). The Future of Biorefining Agricultural Biomass (No. 7624). Farm Foundation.

*Primary Examiner* — James Martinell
(74) *Attorney, Agent, or Firm* — Tyler J. Sisk; Casimir Jones S.C.

(57) ABSTRACT

The present invention relates to compositions and methods for the conversion of lignocellulosic material to fermentable sugars and to products produced therefrom (e.g., ethanol, foodstuffs, etc.). In particular, the invention provides lignocellulose-degrading compositions (e.g., generated via incubation of microbes with lignocellulosic priming feedstock in solid-state fermentation format) and methods of using the same (e.g., in saccharification and/or hydrolysis steps (e.g., on ethanologenic feedstock) and as food or feed additives).

11 Claims, 7 Drawing Sheets

COMPOSITIONS AND METHODS FOR CONVERSION OF LIGNOCELLULOSIC MATERIAL TO FERMENTABLE SUGARS AND PRODUCTS PRODUCED THEREFROM

This application claims priority to U.S. Provisional Patent Application Ser. No. 61/160,969, filed Mar. 17, 2009, hereby incorporated by reference in its entirety.

FIELD OF THE INVENTION

The present invention relates to compositions and methods for the conversion of lignocellulosic material to fermentable sugars and to products produced therefrom (e.g., ethanol, foodstuffs, etc.). In particular, the invention provides lignocellulose-degrading compositions (e.g., generated via incubation of microbes with lignocellulosic priming feedstock in solid-state fermentation format) and methods of using the same (e.g., in saccharification and/or hydrolysis steps (e.g., on ethanologenic feedstock) and as food or feed additives).

BACKGROUND OF THE INVENTION

Renewable transportation fuels are of significant scientific, economic, environmental, and geopolitical interest due to the inherently limited supply of petroleum. Among renewable transportation fuel alternatives, large-scale generation of ethanol from lignocellulosic starting material has several advantages including a ready supply of feedstock, potential to reduce greenhouse gas emissions (e.g., depending on cultivation, harvesting, and processing methods), potential for job creation particularly in rural settings, current and projected availability of flex-fuel and dedicated ethanol-fueled vehicle technology, and distribution systems already amenable to volatile liquid fuels. However, current methods for lignocellulosic ethanol production have unfavorable chemical and/or energy requirements and therefore unacceptable cost of production, largely due to the recalcitrance of lignocellulosic feedstock to saccharification and hydrolysis in comparison to starch-rich feedstock such as milled corn kernels (See e.g., Sun et al. (2002) *Bioresource Technol.* 83:1-11; Hahn-Hagerdal et al. (2006) *Trends Biotechnol.* 24:549-556; Sanchez et al. (2007) *Bioresource Technol.* 99:5270-5295; each herein incorporated by reference in their entireties).

Biochemically, the major impediment to the economical use of lignocellulosic feedstock is the presence of hemicelluloses and lignins surrounding and/or cross-linking cellulose. In order for cellulase enzymes to efficiently access and degrade cellulose during the fermentation step, these hemicelluloses and lignins must have previously been at least partially degraded. For this reason, pretreatment of lignocellulosic feedstock is currently considered an economically unfortunate necessity.

Through pretreatment, feedstock is modified chemically, morphologically, and/or physically. Pretreatment methods standard in the art include exposure of lignocellulosic feedstock to high temperature and/or pressure (as with steam pretreatment or hydrothermolysis), acids or bases, or a combination of such methods (See e.g., Galbe et al. (2007) *Adv. Biochem. Engin./Biotechnol.* 108:41-65; Chandra et at (2007) *Adv. Biochem. Engin./Biotechnol.* 108:67-93; each herein incorporated by reference in their entireties). However, each of these pretreatment approaches has drawbacks. Dilute acid pretreatment (generally at high temperature, e.g. 140-200° C.) hydrolyzes hemicelluloses yielding a significant proportion of monomer sugars, but acid-hydrolyzed materials are generally difficult to ferment due to the generation of compounds that are toxic to microbes used for fermentation (See e.g., Galbe and Zacchi (2007) *Adv. Biochem. Engin./Biotechnol.* 108:41-65; Chandra et at (2007) *Adv. Biochem. Engin./Biotechnol.* 108:67-93; each herein incorporated by reference in their entireties). Alkaline pretreatment (also generally conducted at high temperature) causes at least partial delignification and solubilization of hemicelluloses as well as greater accessibility of the crystalline cellulose component of the cell wall; however, alkaline pretreatment is not suitable for all lignocellulosic feedstock types (See e.g., Galbe et al. (2007) *Adv. Biochem. Engin./Biotechnol.* 108:41-65; herein incorporated by reference in its entirety). Furthermore, a washing or pH adjustment step may be required for acid- or alkaline-pretreated materials to facilitate compatibility with downstream fermentation processes intolerant of low or high pH. Steam pretreatment and combinations of steam and pH treatments such as ammonia fiber explosion (AFEX) are technologies closest to commercial production, but again are not suitable for all feedstock types and have high energetic demands (See e.g., Galbe and Zacchi (2007) *Adv. Biochem. Engin./Biotechnol.* 108:41-65; herein incorporated by reference in its entirety). Hydrothermolysis treatment requires lower initial energy investment than steam pretreatment, but results in the need for more energy-demanding downstream processes (See e.g., Galbe and Zacchi (2007) *Adv. Biochem. Engin./Biotechnol.* 108:41-65; herein incorporated by reference in its entirety). Wet oxidation pretreatment (infusion of biomass with water and air or oxygen at 120° C.) is only compatible with low-lignin feedstock and renders unrecoverable any lignin that is present; this is considered detrimental from a process standpoint, as this lignin might otherwise be used as solid fuel within the biorefinery (See e.g., Galbe and Zacchi (2007) *Adv. Biochem. Engin./Biotechnol.* 108:41-65; herein incorporated by reference in its entirety). A further consideration is the ability to utilize residual material from biofuel production for other purposes, such as agricultural feed additives. Such secondary uses would offer economic benefit by lowering the cost of agricultural food and feed while simultaneously preventing the cost of biofuel residue disposal. However, this is generally impossible for existing technologies that render residual material unfit for consumption due to the presence of solvents, acids, bases, or by resulting in residuals that are of poor or even anti-nutritive value.

SUMMARY OF THE INVENTION

The present invention relates to compositions and methods for the conversion of lignocellulosic material to fermentable sugars and to products produced therefrom (e.g., ethanol, foodstuffs, etc.). In particular, the invention provides lignocellulose-degrading compositions (e.g., generated via incubation of microbes with lignocellulosic priming feedstock in solid-state fermentation format) and methods of using the same (e.g., in saccharification and/or hydrolysis steps (e.g., on ethanologenic feedstock) and as food or feed additives).

Accordingly, in some embodiments, the present invention provides compositions comprising lignocellulose-degrading compositions, methods of generating lignocellulose-degrading compositions, and methods of utilizing the lignocellulose-degrading compositions. In some embodiments, the invention provides methods of generating lignocellulose-degrading compositions utilizing a priming step. In some embodiments, the priming step comprises solid state fermentation. In some embodiments, a microbe with lignocellulose-degrading capacity is incubated with priming feedstock. The present invention is not limited by the type or source of priming feedstock. In some embodiments, the priming feedstock is lignocellulosic in nature. In some embodiments, the lignocellulosic priming feedstock is a natural material. Natural lignocellulosic materials utilized as a priming feedstock include but are not limited to spent brewer's grain, forest residue, mill waste, urban wood waste, agricultural residues, and bioenergy crops. In some embodiments, spent brewer's grain is in the form of dried distillers grains (DDG). In some embodiments, spent brewer's grain is in the form of dried distillers grains with solubles (DDGS). In some embodiments, the natural lignocellulosic materials comprise corn stover, corn husks, corn cobs, corn fiber, wheat straw, milo stubble, switchgrass, deciduous wood, coniferous wood, deciduous or coniferous wood chips, deciduous or coniferous sawdust, citrus waste, urban green waste or residue, food manufacturing industry waste or residue, cereal manufacturing waste or residue, hay, straw, rice straw, sugarcane, sugarcane bagasse, grain cleanings, rice hulls, barley straw, *salix*, spruce, poplar, eucalyptus, *Brassica carinata* residue, *Antigonum leptopus*, sweetgum, *Miscanthus*, *Sericea lespedeza*, Chinese tallow, hemp, rapeseed, *Sorghum bicolor*, soybean leaves, soybeans stems, soybean pods, soybean residue, sunflower leaves, sunflower stems, seedless sunflower heads, sunflower hulls, sunflower residue, Arundo, nut shells, deciduous leaves, cotton fiber, manure, coastal Bermuda grass, clover, Johnsongrass, flax, buckwheat straw, oat straw, millet straw, amaranth straw, amaranth stems, amaranth leaves, amaranth residue, spelt straw, rye straw, alfalfa, and/or bamboo. In some embodiments, one two, three, four or more types of lignocellulosic material is used as priming feedstock. In some embodiments, the lignocellulosic priming feedstock is derived from a recombinant, transformed, transfected, transgenic, mutant, or otherwise genetically altered organism. In some embodiments, the lignocellulosic priming feedstock is a synthetic material. In some embodiments, the synthetic material comprises one or more components of plant cell walls such as cellulose, xyloglucan, arabinoxyloglucan, glucuronoarabinoxylan, xylan, arabinoxylan, polygalacturonans, homogalacturonons, rhamnogalacturonon I, rhamnogalacturonan II, apiogalacturonan, mannan, callose, mixed-linkage glucans (also known as (1→3),(1→4) βglucans), callose, glucuronomannans, hydroxyproline-rich glycoproteins, arabinogalactan proteins, glycine-rich proteins, proline-rich proteins, extensin, or lignins. In some embodiments, the plant cell wall components are fragmented or truncated relative to their length in natural plant cell walls. In some embodiments, the lignocellulosic priming feedstock is corn stover. In some embodiments, the lignocellulosic priming feedstock is corn cob.

In some embodiments, lignocellulosic priming material is processed to result in a smaller particle size relative to its starting state. For example, particle diameter may be 0.05-0.1 mm, 0.1-0.5 mm, 0.5-1.0 mm, 1.0-2.5 mm, 2.5-5.0 mm, 5.0-10.0 mm, 10.0-25.0 mm, 25.0-50 mm, smaller than 0.05 mm or larger than 50 mm. The present invention is not limited to any particular method of generating a desired particle size. In some embodiments, use of hammer mills, knife mills, ball mills, chipping machines, grinding machines, extrusion machines, and/or irradiation are utilized to generate a particle diameter of a desired size. Methods of generating a desired particle size are known in the art. In some embodiments, particle size reduction of lignocellulosic priming feedstock occurs within atmospheric ranges of temperature and pressure. In some embodiments, particle size reduction of lignocellulosic priming feedstock occurs at low temperature. In some embodiments, low temperature is 0° C. to −20° C., −20° C. to −50° C., −50° C. to −100° C., −100° C. to −200° C., or colder. In some embodiments, the water content of the lignocellulosic material is reduced prior to particle size reduction.

In some embodiments, lignocellulosic priming feedstock is incubated with at least one lignocellulose-degrading microbe (e.g., to generate a lignocellulosic feedstock degradation composition of the invention). In some embodiments, the microbe is a fungus. In some embodiments, the microbe is a filamentous fungus. The present invention is not limited by the type of filamentous fungus utilized. Indeed, a variety of filamentous fungi find use in the invention including, but not limited to, species of the genera *Trichoderma, Gliocladium, Aspergillus, Rhizopus, Clostridium, Phanerochaete, Bacillus, Penicillium, Aureobasidium, Humicola, Talaromyces, Chrysosporium, Monilia, Paecilomyces*, and *Pleurotus*. In some embodiments, the microbe is a brown rot fungus. In some embodiments, the microbe is a white rot fungus. In some embodiments, the microbe is a soft rot fungus. In some embodiments, the microbe is a yeast. In some embodiments, the microbe is a species of bacteria. In some embodiments, the microbe is a recombinant, transformed, transfected, transgenic, mutant, or otherwise genetically altered strain. In some embodiments, more than one microbe is incubated with lignocellulosic priming feedstock. In some embodiments, the microbe is present on the lignocellulosic material prior to processing (e.g., the lignocellulosic priming feedstock is not sterile). In some embodiments, the lignocellulose-degrading microbe is *Aspergillus niger*. In some embodiments, the lignocellulose-degrading microbe is *Aspergillus niger* var. *altipes* (ATCC 10549; IFO 4067; MUCL 13608; WB 4863). In some embodiments, the microbe is a strain of *Aspergillus oryzae*. In some embodiments, the microbe is a strain of *Rhizopus oligosporus* (also known as *Rhizopus microsporus* var. *oligosporus*). In some embodiments, the strain of *Rhizopus oligosporus* is strain 2UV3. In some embodiments, two or more lignocellulose-degrading microbes are utilized for incubation with lignocellulosic priming feedstock (e.g., a combination of *Aspergillus oryzae* and *Rhizopus oligosporus* is utilized). In some embodiments, three, four, five or more lignocellulose-degrading microbes are utilized for incubation with lignocellulosic priming feedstock.

In some embodiments, at least one additional component is added to the lignocellulosic material (e.g., to aid fermentation and/or limit bacterial growth). The invention is not limited by the type of additional component added. Additional components include, but are not limited to, water, buffers, nutrient media, surfactants, salts, minerals, osmolytically active agents, fermentation additives, nitrogen sources, antibiotics, and/or carbon sources. In some embodiments, fermentation additives include but are not limited to corn starch, BACTO Peptone (DIFCO), yeast extract, $MgSO_4.7H_2O$, KCl, $KH_2PO_4$, deionized water, and/or LACTOSIDE antibiotic (Ethanol Technology, Milwaukee, Wis.). In some embodiments, an inoculum (e.g., liquid inoculum, dried (e.g., powered) inoculum, or combination thereof comprising one or more lignocellulose-degrading microbes is added to lignocellulosic priming feedstock. In some embodiments, the ratio of liquid inoculum volume to mass of priming feedstock is below 1 ml per 10 g; 1-2 ml per 10 g; 2-4 ml per 10 g; 4-6 ml per 10 g; 6-8 ml per 10 g; 8-10 ml per 10 g; 10-20 ml per 10 g; 20-50 ml per 10 g; 50-100 ml per 10 g. In some embodiments, the ratio of dried inoculum mass to mass of priming feedstock about 1:1, about 1:5, about 1:10, about 1:20, about 1:50, about 1:100, about 1:200, about 1:500, about 1:1000, about 1:2500, about 1:5000, about 1:10000, about 1:20000, about 1:50000, or ratios between, below or above these amounts. In some embodiments, 15% yeast extract is added.

In some embodiments, lignocellulosic priming feedstock (e.g., processed to generate a desired feedstock particle size) is inoculated with one or more strains of lignocellulose-degrading microbes (e.g., to generate a lignocellulosic feedstock degradation composition) without limitation to the method of inoculation or method of preparing the inoculum. In some embodiments, the one or more lignocellulose-degrading microbes and lignocellulosic priming feedstock are spread on a solid support (e.g., a stainless steel tray) to create a bed. In some embodiments, the bed height is below 0.5 cm; 0.5-1 cm; 1-5 cm; 5-10 cm; 10-20 cm; 20-50 cm; 50-100 cm; 100-1000 cm; 1000 cm or more. In some embodiments, alternative fermentation apparatus devices are used, including but not limited to columns, reactor vessels, Koji-type shallow tray reactors, stationary tower reactors, rotating drum reactors, and/or rocking reactors. In some embodiments, one or more lignocellulose-degrading microbes and lignocellulosic priming feedstock are incubated at a temperature, pressure, $O_2$ level, aeration level, relative humidity, pH, and for a duration of time sufficient for production of at least one lignocellulose-degrading composition. The invention is not limited by the duration of the incubation. For example, the duration of the incubation may be 1 h; 2 h; 5 h; 10 h; 20 h; 1 day; 1-5 days; 5-10 days; 10-20 days; 20-30 days; 30-50 days; 50-100 days; 100-300 days or more. In some embodiments, the incubation is conducted for 5 days. The incubation may be conducted at a relative humidity of 1%; 1-10%; 10-25%; 25-50%; 50-75%; or 75-99%. In some embodiments, the relative humidity of the incubation is 50%. The incubation may be conducted at 10° C.; 10-20° C.; 20-40° C.; 40-60° C.; 60-80° C.; 80-120° C., or at a temperature below 10° C. or above 120° C. In some embodiments, the incubation is conducted at 30° C.

In some embodiments, the present invention provides compositions for degradation of lignocellulosic feedstock. In some embodiments, the lignocellulosic feedstock degradation composition comprises one or more lignocellulose-degrading microbes and a lignocellulosic priming feedstock (e.g., incubated at a temperature, pressure, $O_2$ level, aeration level, relative humidity, pH, and/or for a duration of time sufficient for production of at least one lignocellulose-degrading composition). The present invention is not limited by any particular mechanism of action of the lignocellulose-degrading composition. Indeed, an understanding of the mechanism of action of a lignocellulase-degrading composition of the invention is not necessary to practice the invention and the invention is not limited to any particular mechanism of action. In some embodiments, a lignocellulase-degrading composition possesses one or more enzymatic activities. The one or more enzymatic activities may comprise, but are not limited to, cellulase, xylanase, endoxylanase, exoxylanase, beta xylosidase, endomannase, beta-mannosidase, beta-mannase, pectin lyase, pectate lyase, endopolygalacturonase, exopolygalacturonase, rhamnohydrolase, xylogalacturonase, alpha-rhamnosidase, rhamnogalacturonan lyase, xylosidase, arabinofuranosidase, arabinofuranohydrolase, endoarabinase, exoarabinase, endogalactanase, glucuronidase, feruloyl esterase, p-coumaroyl esterase, galactosidase, endoglucanase, exoglucanase, protease, lipase, glucoamylase, cellobiohydrolase, alpha amylase, acetyl esterase, methyl esterase, lignin peroxidase, and/or laccase. In some embodiments, the lignocellulose-degrading compositions comprise proteinaceous components. In some embodiments, the lignocellulose-degrading composition comprises nucleic acid polymers. In some embodiments, the lignocellulose-degrading composition comprises ribozymes. In some embodiments, the lignocellulase-degrading composition comprises organic compounds. In some embodiments, the lignocellulose-degrading composition comprises inorganic compounds. In some embodiments, the lignocellulose-degrading composition comprises one or more active agents (e.g., osmolytically active agents, fermentation additives, and/or antibiotics).

In some embodiments, the present invention provides a method of producing ethanol comprising saccharification and/or fermentation of an ethanologenic (e.g., lignocellulosic) feedstock utilizing a lignocellulose-degrading composition comprising one or more lignocellulose-degrading microbes and a lignocellulosic priming feedstock. In some embodiments, the lignocellulosic component of the ethanologenic feedstock is corncob. In some embodiments, the corncob has 0-2% moisture; 2-4% moisture; 4-9% moisture; 9-15% moisture; 15-25% moisture or a moisture level above 25%. In some embodiments, the ethanologenic feedstock comprises starch-rich material. Starch-rich materials are known in the art and include but are not limited to grains, storage roots, tubers, nuts, and fruits, and more specifically may be grain, kernels, or flours of corn (maize), wheat, rice, oats, barley, rye, amaranth, buckwheat (spelt), potato, sweet potato, taro, yam, cassava, tapioca, arrowroot, cassava, legumes, chestnut, arracacha, banana, kudzu, oca, sago, and sorghum. In some embodiments, the starch-rich material is a residue or byproduct from the food, feed, or beverage manufacturing industry or paper industry. In some embodiments, the starch-rich component of the ethanologenic feedstock is derived from a recombinant, transformed, transfected, transgenic, mutant, or otherwise genetically altered organism. In some embodiments, the starch-rich component of the ethanologenic feedstock comprises a processed or purified material including but not limited to starch, dextran, glucose, or cellobiose. In some embodiments, the starch-rich component of the ethanologenic feedstock comprises corn kernels. In some embodiments, the corn kernels are US #2, yellow dent (e.g., containing 12% moisture). In some embodiments, the ethanologenic feedstock comprises a mixture of lignocellulosic and starch-rich material. The proportion of lignocellulosic and starch-rich material may be varied to yield optimal levels of ethanol production. For example, in some embodiments, lignocellulosic material content may comprise about 1%; 1-5%; 5-10%; 10-20%; 50-75%; or 75-100% of the ethanologenic feedstock. In some embodiments, the lignocellulosic material content of the ethanologenic feedstock is 30%.

In some embodiments, the ethanologenic feedstock is subjected to a cooking step prior to saccharification. In some embodiments, the ethanologenic feedstock is processed (e.g., utilizing a size decreasing method described herein (e.g., hammer mill, knife mill, ball mill, chipping machine, grinding machine, etc.)) to result in a smaller ethanologenic feedstock particle size prior to cooking. In some embodiments, ethanologenic feedstock particle diameter is below 0.05 mm, 0.05-0.1 mm, 0.1-0.5 mm, 0.5-1.0 mm, 1.0-2.5 mm, 2.5-5.0 mm, 5.0-10.0 mm, 10.0-25.0 mm, 25.0-50 mm, below 0.05 mm or greater than 50 mm. In some embodiments, the ethanologenic material is ground using a hammer mill. In some embodiments, the hammer mill is fitted with a screen (e.g., a #4 screen (e.g., with 1.588 mm mesh openings)). In some embodiments, a slurry is formed by appropriate addition of ethanologenic feedstock to a liquid. In some embodiments, the slurry is formed by first adding a starch-rich component of the ethanologenic feedstock to the liquid (e.g., followed by adding a lignocellulosic component). In some embodiments, the slurry is formed by first adding a lignocellulosic component of the ethanologenic feedstock to the liquid (e.g., followed by adding a starch rich component). In some embodiments, the starch-rich component of the ethanologenic feedstock is cooked in the absence of the lignocellulosic component. In some embodiments, the ethanologenic feedstock is sterilized prior to processing. In some embodiments, sterilization is achieved by autoclaving (e.g., at 121° C.). In some embodiments, sterilization is achieved by other means including but not limited to gamma irradiation, electron beam irradiation, microwave irradiation, dry heat, and visible light irradiation such as ultraviolet and infrared irradiation, aseptic filtration, and/or application of bacteriocidal and/or fungicidal agents (e.g., in a solid, liquid or gaseous form). In some embodiments, alpha-amylase is added to the starch-rich component of the ethanologenic feedstock, followed by incubation at a temperature sufficient for activity of the alpha-amylase. For example, in some embodiments, 0.06% alpha-amylase (by weight of grain) is added to ground corn, followed by heating to 85° C. for five minutes. In some embodiments, the amount of alpha-amylase added is 0.001%-0.02%; 0.02%-0.04%; 0.04%-0.06%; 0.06%-0.1%; 0.1%-5%; 5% or more by weight of dry matter of the substrate. In some embodiments, heating of the starch-rich component to which alpha-amylase has been added is carried out (e.g., at 85° C. for 1-2 min; 2-5 min; 5-10 min; 10-20 min; 20-60 min; 60 min or more). In some embodiments, the alpha-amylase is SPEZYME XTRA (Genencor, Rochester, N.Y., USA). In some embodiments, the lignocellulosic component of the ethanologenic feedstock is added slowly to the amylase-treated starch-rich component of the ethanologenic feedstock. For example, in some embodiments, ground corn cob is added slowly to the ground corn mash and the mixture heated (e.g., at 85° C. for 20 minutes). In some embodiments, the ethanologenic feedstock mash is agitated vigorously throughout the cooking step. In some embodiments, the mash is stirred at 350 rpm using an SC3 blade present in a fermenter bioreactor vessel. In some embodiments, the mash is sterilized. In some embodiments, the mash is heated to 121° C. for 20 minutes and subsequently cooled. In some embodiments, additional alpha-amylase is added to the mash. In some embodiments, 0.04% (by weight of grain) is added to the mash. In some embodiments, the mash is further incubated at a temperature sufficient for activity of the alpha-amylase. In some embodiments, the mash is cooked at 85° C. for 60 minutes. In some embodiments, the further incubation at 85° C. is conducted for 2-5 minutes; 5-10 minutes; 10-20 minutes; 20-60 minutes; 60-120 minutes; 120-360 minutes; 360 minutes or more.

In some embodiments, the present invention provides a method of producing ethanol from lignocellulosic feedstock comprising saccharification of cooked mash containing ethanologenic feedstock using a lignocellulose-degrading composition. In some embodiments, the lignocellulose-degrading composition content of the saccharification mash is 0.1-0.5%; 0.5-1%; 1-5%; 5-10%; 10-20%; 50-75%; or 75-100%. In some embodiments, the lignocellulose-degrading composition accounts for about 1-2%, 2-4%, 4-8%, 8-15% or more of the solids in the saccharification mash. In some embodiments, the lignocellulose-degrading composition accounts for about 5% of the solids in the saccharification mash. In some embodiments, the starch-rich component of the ethanologenic feedstock accounts for about 15-25%, about 25-50%, about 50-70%, 70-90% or more of the solids within the saccharification mash. In some embodiments, the starch-rich component of the ethanologenic feedstock accounts for about 70% of the solids within the saccharification mash. In some embodiments, the lignocellulosic component of the ethanologenic feedstock accounts for about 2-5%, about 5-10%, about 10-20%, about 20-40%, about 40-60%, about 60-80% or more of the solids in the saccharification mash. In some embodiments, the lignocellulosic component of the ethanologenic feedstock accounts for about 25% of the solids in the saccharification mash. In some embodiments, the saccharification mash contains a total solids content of about 5%, about 10%, about 15% about 20%, about 30%, about 40%, about 50% or more. In some embodiments, the saccharification mash contains a total solids content of about 30%. In some embodiments, the saccharification mash is agitated vigorously during the addition of each component. For example, in some embodiments, the mash is stirred at 350 rpm using an SC3 blade present in a fermenter bioreactor vessel.

In some embodiments, saccharification and fermentation occur in separate steps. In some embodiments, saccharification and fermentation occur simultaneously (e.g., in the same container). In some embodiments, ethanol is produced from an ethanologenic feedstock via addition of glucoamylase to a mash comprising the enthanologenic feedstock. In some embodiments, 0.06% glucoamylase (by weight of starch-rich component of the ethanologenic feedstock) is added to the mash. In some embodiments, a nitrogen source is added to a mash comprising the enthanologenic feedstock. Nitrogen sources are known in the art and include but are not limited to urea; peptones; enzymatic digests or hydrolysates of meat, casein, soymeal, or gelatin; tryptone; phytone; nitrate; and ammonium. In some embodiments, urea is used as a nitrogen source. In some embodiments, urea is added at a concentration of 1 g/L mash. In some embodiments, a mash comprising a saccharified enthanologenic feedstock is inoculated with an ethanologenic agent without limitation to the method of inoculation. In some embodiments, the ethanologenic agent is a microbe. Ethanologenic microbes include but are not limited to species of the genera *Saccharomyces*, *Zymomonas*, *Kluyveromyces*, *Brettanomyces*, *Pichia*, *Candida*, *Escherichia*, *Klebsiella*, *Fabospora*, *Pachysolen*, *Clostridium*, *Thermoanaerobacter*, *Mucor*, *Chalara*, *Monilia*, *Neurospora*, *Aspergillus*, *Trichoderma*, *Paecilomyces*, *Spirochaeta*, *Erwinia*, *Leuconostoc*, *Streptococcus*, *Fusarium*, *Thermus*, and *Piromyces*. In some embodiments, the ethanologenic microbe is recombinant, transformed, transfected, transgenic, mutant, or otherwise genetically altered. In some embodiments, more than one type of ethanologenic microbe is used. In some embodiments, the ethanologenic microbe is a yeast. In some embodiments, the ethanologenic microbe is *Saccharomyces cerevisiae*. In some embodiments, the ethanologenic microbe is *Saccharomyces cerevisiae* SUPERSTART (Ethanol Technology, Milwaukee, Wis., USA). In some embodiments, the ethanologenic microbe is *Saccharomyces cerevisiae* THERMOSACC (Ethanol Technology, Milwaukee, Wis.). In some embodiments, inoculation is performed by adding 30 million cells per gram ethanologenic feedstock. In some embodiments, the ethanologenic microbe is added as an active dry yeast preparation. In some embodiments, active dry yeast are added with a cell count of below $1\times10^9$ cells/g, 1 to $5\times10^9$ cells/g, 5 to $10\times10^9$ cells/g, 10-20$\times$ $10^9$ cells/g, 20 to $50\times10^9$ cells/g, $50\times10^9$ cells/g or above. In some embodiments, the ethanologenic microbe is added as a wet cake preparation. In some embodiments, wet cake preparations of active yeast are added at a cell count of $1\times10^9$ cells/g, 1 to $5\times10^9$ cells/g, 5 to $10\times10^9$ cells/g, 10-20$\times10^9$ cells/g, 20 to $50\times10^9$ cells/g, $50\times10^9$ cells/g or above. In some embodiments, viability of ethanologenic microbe is determined or known prior to addition to the fermentation. Viability may be 50% or below, 50-75%, 75-85%, 85-95%, 95-99%, 99% or above. In some embodiments, incubation is performed at a temperature sufficient to cause ethanol production by the ethanologenic microbe.

In some embodiments, the incubation occurs at a temperature, pressure, $O_2$ level, aeration level, relative humidity, pH, and for a duration of time sufficient for production of ethanol by the ethanologenic microbe. For example, in some embodiments, incubation is conducted at 10° C.; 10-20° C.; 20-40° C.; 40-60° C.; 60-80° C.; 80-120° C., or above. In some embodiments, the incubation is conducted at 34° C. In some embodiments, the incubation is conducted at 30° C. In some embodiments, the duration of the incubation is 1 h; 2 h; 5 h; 10 h; 20 h; 1 day; 1-5 days; 5-10 days; 10-20 days; 20-30 days; 30-50 days; 50-100 days; 100-300 days or more. In some embodiments, the incubation is conducted for 48 h. In some embodiments, the incubation is conducted for 72 h. In some embodiments, at least one additional component is added to the mash. In some embodiments, a component that assists saccharification and/or fermentation is added. The present invention is not limited by the component that assists saccharification and/or fermentation that is added to the incubation. Indeed a variety of components that assists saccharification and/or fermentation can be utilized including, but not limited to water, buffers, nutrient media, surfactants (including but not limited to TWEEN-20, TWEEN-80, polyoxyethylene glycol, TWEEN 81, Emulgen 147, amphoteric anhitole 20BS, cationic Q-86W, sophorolipid, rhamnolipid, and bacitracin), salts, minerals, osmolytically active agents, purified or crude enzymes, nitrogen sources, antibiotics (including but not limited to LACTOSIDE (Ethanol Technology, Milwaukee, Wis.)), and carbon sources.

In some embodiments, ethanol and fermentation residues are separated and collected. Materials and Methods useful for separation are known in the art and include but are not limited to distillation and molecular sieve technologies. In some embodiments, fermentation residues are utilized for purposes including but not limited to animal feed additives, heat generation, power generation, and precursors for synthetic chemical products.

In some embodiments, a lignocellulose-degrading composition of the invention is utilized for improving the nutritional quality of lignocellulosic feedstock. In some embodiments, a lignocellulose-degrading composition is generated by a method comprising inoculating a lignocellulosic feedstock with at least one filamentous fungus and subsequently fermenting the fibrous by-product or residue whereby a dry matter content of the by-product or residue decreases, a protein content of the by-product or residue increases, and a fat content of the by-product or residue decreases. The invention is not limited by the type of filamentous fungus utilized. A variety of filamentous fungi may be used including, but not limited to *Rhizopus, Aspergillus, Trichoderma*, and any combination thereof. Similarly, the invention is not limited by the type of lignocellulosic priming feedstock or fibrous by-produce or residue. A variety of lignocellulosic priming feedstocks or fibrous by-products or residues may be utilized including, but not limited to spent brewer's grains, dried distiller's grains, dried distiller's solubles, distiller's dried grains with solubles, residues of the cereal processing industry, wheat bran, soybean hulls, citrus pulp, beet pulp, quinoa, rice husks or hulls, bagasse, apple pommace, and/or mixtures thereof. In some embodiments, the dry matter content of the fermented lignocellulosic feedstock is decreased by about 7% to about 12%, and/or the protein content is increased by about 10% to about 15%, and/or the fat content is decreased by about 40% to about 50%. In some embodiments, fiber (neutral detergent fiber; NDF) content decreases by about 10% to about 15%. One of skill in the art appreciates that different animals have differing optimal requirements for these nutrients, and altering fermentation times and conditions allows tailoring the final fermented product in accordance with nutritive needs. In some embodiments, a fermentation step is conducted as a solid-state fermentation, using the fibrous byproduct or residue as a substrate for growth of the filamentous fungus, as described herein. Additional suitable reactors and conditions for such solid state fermentations are known in the art.

The present invention also provides compositions comprising foodstuffs (e.g., animal feeds and/or feed supplements) comprising lignocellulosic feedstock components and methods of generating the same. For example, in some embodiments, the invention provides a method comprising inoculating a lignocellulosic feedstock with at least one filamentous fungus; fermenting the fibrous by-product or residue whereby a dry matter content of the lignocellulosic feedstock decreases and/or a protein content of the lignocellulosic feedstock increases and/or a fat content of the lignocellulosic feedstock decreases; separating at least one enzyme from the fermented fibrous by-product or residue; and recovering the lignocellulose-degrading composition and/or the separated enzyme (e.g., for use as a foodstuff (e.g., animal feed and/or supplement) that fed to an animal). In some embodiments, a separated enzyme is utilized to increase digestibility in an animal and/or to increase the nutritive values of a foodstuff. In some embodiments, a separated enzyme is utilized in the brewing and/or distilling industry (e.g., for use in fermentation processes). For example, in some embodiments, an enzyme produced and separated as described herein (e.g., on a byproduct or residue of the brewing or distilling industry), is utilized in brewing or distilling fermentations comprising the substrate (e.g., lignocellulosic feedstock), as it was specifically produced by the organism to digest that substrate (e.g., lignocellulosic feedstock). In some embodiments, the separated enzyme is of fungal origin. In some embodiments, the separated enzyme is a protease.

The invention also provides an enzyme-containing animal feed or feed supplement comprising a lignocellulose-degrading composition. In some embodiments, the enzyme-containing animal feed or feed supplement comprising a lignocellulose-degrading composition is produced by inoculating a fibrous byproduct or residue of a food manufacturing process with at least one filamentous fungus and fermenting the fibrous byproduct or residue. In some embodiments, the inoculating and fermenting results in a dry matter content of the byproduct or residue decreasing, and/or a protein content of the byproduct or residue increasing, and/or a fat content of the byproduct or residue decreasing, and/or at least one enzyme of fungal origin introduced into the fermented byproduct or residue. In some embodiment, the feed or feed supplement is utilized for animal nutrition.

The invention also provides a method of improving body weight gain rate of a growing animal, comprising feeding a nutritionally effective amount of an enzyme-based animal feed supplement formulated by the steps of inoculating a lignocellulosic feedstock with at least one microbe (e.g., at least one filamentous fungus), fermenting the lignocellulosic feedstock whereby a dry matter content of the byproduct or residue decreases, and/or a protein content of the byproduct or residue increases, and/or a fat content of the byproduct or residue decreases; separating at least one enzyme from the fermented fibrous byproduct or residue; dewatering the separated enzyme; and providing the dewatered enzyme to an animal in a formulation comprising a suitable carrier. Fibrous by-products or residues and fungi are as described herein. In some embodiments, the feed or feed supplement is provided to any animal, including but not limited to humans, avian, bovine, porcine, equine, ovine, caprine, canine, feline, piscine, camelid, rodent species as well as fish and shellfish subjects.

DEFINITIONS

Figure 1:
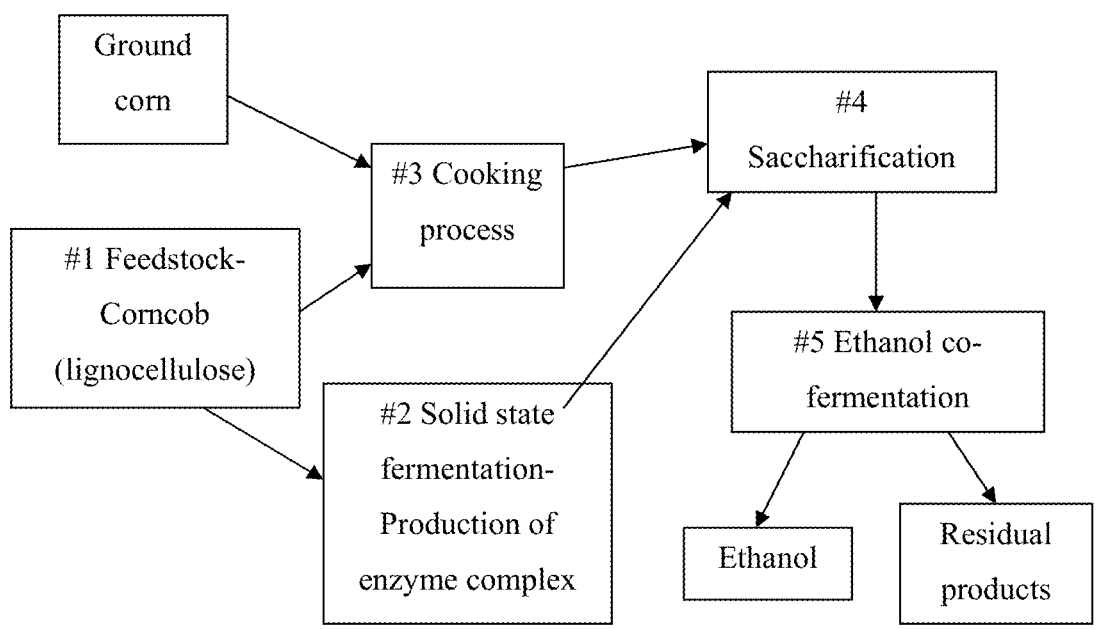
FIG. 1 shows a flowchart depicting a process for an integrated biorefinery producing ethanol from lignocellulosic feedstocks in an embodiment of the present invention.

To facilitate understanding of the invention, a number of terms are defined below.

As used herein, the term "pretreatment" refers to any physical, chemical, or mechanical process applied to feedstock material prior to use of the feedstock (e.g., for generation of ethanol) including but not limited to exposure of the feedstock to acids, bases, high pressure, low pressure, steam, water heated to at least 99° C., oxidizing agents, organic solvents, irradiation, pyrolysis, ammonia fiber explosion (AFEX), $CO_2$ explosion, ozonolysis, wet oxidation, or a combination thereof. Pretreatment does not include mechanical processing conducted solely to reduce particle size of substrate or feedstock material. Those skilled in the art recognize that lignocellulosic materials arising from the paper industry (such as recycled paper, paper pulp, and paper sludge), while compatible with methods of the present invention, have inherently undergone processing treatments prior to their use as substrates for fermentation.

As used herein, the terms "lignocellulose-degrading composition" and "lignocellulosic feedstock degradation composition" refer to a composition comprising a lignocellulosic priming feedstock inoculated with one or more strains of lignocellulose-degrading microbes (thereafter, e.g., incubated at a temperature, pressure, $O_2$ level, aeration level, relative humidity, pH, and/or for a duration of time described herein). A lignocellulose-degrading composition, when added to a saccharification or simultaneous saccharification and fermentation process, results in increased ethanol production from lignocellulosic feedstock than occurs in absence of its addition. The lignocellulose-degrading compositions of the present invention are not limited to any particular mechanism of action and an understanding of the mechanism of action is not necessary to practice the invention. In some embodiments, lignocellulose-degrading compositions comprise enzymatic activity. Enzymatic activities of a lignocellulose-degrading composition may include but are not limited to cellulase, xylanase, endoxylanase, exoxylanase, beta xylosidase, endomannase, beta-mannosidase, beta-mannase, pectin lyase, pectate lyase, endopolygalacturonase, exopolygalacturonase, rhamnohydrolase, xylogalacturonase, alpha-rhamnosidase, rhamnogalacturonan lyase, xylosidase, arabinofuranosidase, arabinofuranohydrolase, endoarabinase, exoarabinase, endogalactanase, glucuronidase, feruloyl esterase, p-coumaroyl esterase, galactosidase, endoglucanase, exoglucanase, protease, lipase, glucoamylase, cellobiohydrolase, alpha amylase, acetyl esterase, methyl esterase, lignin peroxidase, and laccase.

As used herein, the terms "priming feedstock" and "lignocellulosic priming feedstock" refer to material used as substrate for generation of at least one lignocellulose-degrading composition.

As used herein, the term "dried distillers grains" (DDG) refer to waste material generated by the distilling or brewing industry that is produced by a) alcohol fermentation, b) distillation of the fermented mash to remove the alcohol, c) processing the remaining slurry containing e.g., 5-10% dry matter by screening and pressing or centrifuging to remove the coarser particles, d) drying the remaining particles, which are then referred to as DDG. As used herein, the term "dried distillers grains with solubles" (DDGS) is defined as waste material generated by the distilling industry in which the soluble material extracted in step c) above is evaporated to form a syrup containing e.g., 30-40% dry matter, which is then added back to DDG and the entire mixture dried to produced DDGS.

As used herein, the term "ethanologenic feedstock" refers to material used as substrate for the production of ethanol in a saccharification and/or fermentation reaction.

As used herein, the term "lignocellulosic component" is material used as substrate for a fermentation process and that is not rich in starch (wherein the starch content is below about 60% on a dry matter basis). Lignocellulosic components include but are not limited to forest residue, mill waste, urban wood waste, agricultural residues, and bioenergy crops; more specifically, lignocellulosic materials include but are not limited to corn stover, corn husks, corn cobs, corn fiber, wheat straw, milo stubble, switchgrass, deciduous wood, coniferous wood, deciduous or coniferous wood chips, deciduous or coniferous sawdust, citrus waste, urban green waste, hay, straw, rice straw, sugarcane, sugarcane bagasse, grain cleanings, spent brewer's grain including dried distiller's grain (DDG) and dried distiller's grain with solubless (DDGS), rice hulls, barley straw, *salix*, spruce, poplar, eucalyptus, *Brassica carinata* residue, *Antigonum leptopus*, sweetgum, *Miscanthus*, *Sericea lespedeza*, Chinese tallow, hemp, rapeseed, *Sorghum bicolor*, soybean leaves, soybeans stems, soybean pods, soybean residue, sunflower leaves, sunflower stems, seedless sunflower heads, sunflower hulls, sunflower residue, Arundo, nut shells, deciduous leaves, cotton fiber, manure, coastal Bermuda grass, clover, Johnsongrass, flax, buckwheat straw, oat straw, millet straw, amaranth straw, amaranth stems, amaranth leaves, amaranth residue, spelt straw, rye straw, alfalfa, and bamboo. More than one type of lignocellulosic material may be used as components of feedstocks. The lignocellulosic component can be a synthetic material including one or more components of plant cell walls including, but not limited to, cellulose, xyloglucan, arabinoxyloglucan, glucuronoarabinoxylan, xylan, arabinoxylan, polygalacturonans, homogalacturonons, rhamnogalacturonon I, rhamnogalacturonan II, apiogalacturonan, mannan, callose, mixed-linkage glucans (also known as (1→3),(1→4) β-glucans), callose, glucuronomannans, hydroxyproline-rich glycoproteins, arabinogalactan proteins, glycine-rich proteins, proline-rich proteins, extensin, or lignins.

As used herein, the term "starch-rich component" is material used as substrate for a fermentation that is rich in starch (wherein the starch content is equal to or above about 60% on a dry matter basis). Starch-rich materials are known in the art and include but are not limited to grains, storage roots, tubers, nuts, and fruits, and more specifically refer to particles, grain, kernels, or flours of corn (maize), wheat, rice, oats, barley, rye, amaranth, buckwheat, or spelt; potato, sweet potato, taro, yam, cassava, tapioca, arrowroot, cassava, legumes, chestnut, arracacha, banana, kudzu, oca, sago, and sorghum.

As used herein, "lignocellulose-degrading organism" refers to a biological agent or derivative thereof that is capable of generating at least one lignocellulose-degrading composition when combined with a lignocellulosic priming feedstock. Lignocellulose-degrading organisms include but are not limited to microbes including bacteria and fungi (e.g., of the genera *Trichoderma, Gliocladium, Aspergillus, Rhizopus, Clostridium, Phanerochaete, Bacillus, Penicillium, Aureobasidium, Humicola, Talaromyces, Chrysosporium, Monilia, Paecilomyces*, and *Pleurotus* and species comprising whiterot fungi, brown-rot fungi, and soft-rot fungi. Specific examples of lignocellulose-degrading organisms include strains of *Aspergillus niger* (e.g., strain ATCC 10549), *Aspergillus oryzae*, and *Rhizopus oligosporus* (e.g., strain 2UV3). Lignocellulose-degrading organisms may be utilized singly or in combination.

As used herein, "ethanologenic organism" refers to a biological agent or derivative thereof that is capable of producing ethanol upon incubation with ethanologenic feedstock substrate. Ethanologenic organisms include but are not limited to microbes; more specifically, include but are not limited to bacteria and fungi; still more specifically include but are not limited to species of the genera *Saccharomyces, Zymomonas, Kluyveromyces, Brettanomyces, Pichia, Candida, Escherichia, Klebsiella, Fabospora, Pachysolen, Clostridium, Thermoanaerobacter, Mucor, Chalara, Monilia, Neurospora, Aspergillus, Trichoderma, Paecilomyces, Spirochaeta, Erwinia, Leuconostoc, Streptococcus, Fusarium, Thermus*, and *Piromyces*; yet more specifically include but are not limited to strains of *Saccharomyces cerevisiae*; yet more specifically include *Saccharomyces cerevisiae* commercial strains SUPERSTART or THERMOSACC (Ethanol Technology, Milwaukee, Wis.). In some embodiments, the ethanologenic microbe is recombinant, transformed, transfected, transgenic, mutant, or otherwise genetically altered. In some embodiments, more than one type of ethanologenic microbe is used.

The term "culture medium" refers generally to any substance or preparation used for the cultivation of living cells.

The terms "mutated" as used herein, with regard to a gene or gene expression, means that the gene is not a wildtype gene and that the organism does not have a wildtype genotype and/or a wildtype phenotype. The altered gene, genotype or phenotype may be the consequence of a mutation in that gene, or of a gene that regulates the expression of that gene (e.g., transcriptional or post-transcriptional), such that its normal expression is disrupted or extinguished. "Disrupted gene expression" is intended to include both complete inhibition and decreased gene expression (e.g., as in a leaky mutation), below wild-type gene expression.

As used herein, the term "fragment" when used in reference to a sequence (e.g., an amino acid sequence of a protein, a nucleic acid sequence of a gene) represents any amount of the referenced sequence (e.g., 0.001%, 0.1%, 1%, 10%, 30%, 50%, 75%, 80%, 85%, 90%, 95%, 98%, 99.999% of an amino acid sequence or nucleic acid sequence).

The term "genetically altered" as used herein refers to both up-regulation (i.e., activation or stimulation (e.g., by agonizing or potentiating)) and down-regulation (i.e., inhibition or suppression (e.g., by antagonizing, decreasing or inhibiting)). The term "inducible" refers in particular to gene expression which is not constitutive but which takes place in response to a stimulus (e.g., temperature, heavy metals or other medium additive).

The term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

As used herein, the term "transfection" means the introduction of a nucleic acid (e.g., via an expression vector) into a recipient cell by nucleic acid-mediated gene transfer. "Transformation", as used herein, refers to a process in which a cell's genotype is changed as a result of the cellular uptake of exogenous DNA or RNA.

As used herein, the term "transgene" means a nucleic acid (e.g., gene encoding a plant cell wall polysaccharide-degrading enzyme, or an antisense transcript thereto) that has been introduced into a cell. A transgene could be partly or entirely heterologous, i.e., foreign, to the transgenic animal or cell into which it is introduced, or, can be homologous to an endogenous gene of the organism or -cell into which it is introduced, but which is designed to be inserted, or is inserted, into the animal or cell's genome in such a way as to alter the genome of the cell into which it is inserted. A transgene can also be present in a cell in the form of an episome.

The term "vector" refers to a nucleic acid molecule, which is capable of transporting another nucleic acid to which it has been linked. Vectors capable of directing the expression of genes to which they are operatively linked are referred to herein as "expression vectors." The term "expression system" as used herein refers to an expression vector under conditions whereby an mRNA may be transcribed and/or an mRNA may be translated into protein, structural RNA, or other cellular component. The expression system may be an in vitro expression system, which is commercially available or readily made according to art known techniques, or may be an in vivo expression system, such as a eukaryotic or prokaryotic cell containing the expression vector. In general, expression vectors of utility in recombinant DNA techniques are often in the form of "plasmids" which refer generally to circular double stranded DNA loops that, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and are well known in the art or which become known in the art subsequently hereto (e.g., cosmid, phagemid and bacteriophage vectors).

DETAILED DESCRIPTION OF THE INVENTION

The ethanol industry worldwide continues to develop as researchers and industry strive to produce renewable fuels with the biggest return on investment possible. One area where considerable research has been focused is the application and development of compositions for improved fermentation efficiency. Most manufacturers produce compositions comprising enzymes using submerged fermentation (SmF) techniques (See, e.g., Villas-Boas et al. (2002) *Animal Feed Sci. Technol.* 98, 1-12). However, an alternative method, which is becoming increasingly important, is solid state fermentation (SSF) (See, e.g., Krishna (2005) *Crit. Rev. Biotechnol.* 25:1-30; Lonsane et al (1992) Exoenzymes, In: Solid Substrate Cultivation, Mitchell et al., Eds., Elsevier Applied Science, London, pp. 191-209; Pandey et al. (2001) Solid-state fermentation in biotechnology: Fundamentals and applications, Asiatech Publishers, New Delhi, India, p. 221).

SSF can be characterized as the growth of microorganisms on insoluble substrates, with minimal to no free water (See, e.g., Mitchell et al (1992) Definition, characteristics, and potential, In: Solid Substrate Cultivation, Rolz, Ed., Elsevier Applied Science, London, UK, pp. 1-16; Mitchell et al (2006) Solid-state fermentation bioreactors: Fundamentals of design and operation, Springer, Berlin, Germany; Villas-Boas et al. (2002) *Animal Feed Sci. Technol.* 98:1-12). Many bacteria and fungi are capable of growing on solid substrates. However, of these organisms, filamentous fungi are best adapted for these processes due to their physiological characteristics (See, e.g., Mitchell (1992) Microbial basis of process, In: Solid Substrate Cultivation, Rolz, Ed., Elsevier Applied Science, London, UK, pp 17-28). SSF has been widely utilized in Asia for the production of foods and beverages such as soy sauce, sake, and tempeh for centuries (See, e.g., Mudgett (1986) Solid-state fermentations, In: Manual of Industrial Microbiology and Biotechnology, Demain et al., Eds., American Society for Microbiology, Washington, D.C., pp. 66-83; Padmaja et al. (1999) Oriental fermented foods, In: Biotechnology: Food Fermentation, Microbiology, Biochemistry and Technology, Joshi et al., Eds., Educational Publishers and Distributors, New Delhi, India, pp. 523-582).

The present invention relates to compositions and methods for the conversion of lignocellulosic material to fermentable sugars and to products produced therefrom (e.g., ethanol, foodstuffs, etc.). In particular, the invention provides lignocellulose-degrading compositions (e.g., generated via incubation of microbes with lignocellulosic priming feedstock in solid-state fermentation format) and methods of using the same (e.g., in saccharification and/or hydrolysis steps (e.g., on ethanologenic feedstock) and as food or feed additives).

Accordingly, the present invention provides methods that utilize lignocellulose-degrading compositions to saccharify lignocellulosic feedstocks into fermentable carbohydrates in the absence of harsh chemical or physical treatments, and compositions generated using the same. In some embodiments, methods of the invention allow for a co-fermentation process that enables conversion of lignocellulosic degradation products in the presence of fermentable sugars obtained from starch-rich components of ethanologenic feedstock. The lignocellulose-degrading compositions used are produced using a solid state fermentation process on low moisture, solid phase lignocellulosic priming feedstock and specifically selected strains of microbes. In experiments conducted during the development of embodiments of the present invention, filamentous fungi were used as lignocellulose-degrading microbes (See Example 1 and 2). In some embodiments, selected strains of *Aspergillus niger* were used. The present invention provides a fermentation process for ethanol production from ethanologenic feedstock carried out in the presence of low levels (1-10%) of lignocellulose-degrading compositions, a ground starch-rich component of the ethanologenic feedstock, and one or more ethanologenic microbes. In experiments conducted during development of embodiments of the invention, the starch-rich component of the ethanologenic feedstock was ground corn, and the ethanologenic microbe was selected from strains of *Saccharomyces cerevisiae*. While the present invention is not limited to any mechanism of action and while an understanding of the mechanism of action is not necessary to practice the invention, the inhibitory effects of lignin-derived phenolic compounds is minimized by controlling the ratio of the lignocellulosic component and the starch-rich component of the ethanologenic feedstock and by controlling the addition of the lignocellulose-degrading compositions from the solid state fermentation.

In some embodiments, methods of the invention may be used to convert a variety of different fibrous feedstocks to ethanol and other products including compositions that find use as animal food and feed supplements. Fibrous feedstocks include but are not limited to forest residue, mill waste, urban wood waste, agricultural residues, and bioenergy crops. For example, fibrous feedstocks include natural lignocellulosic materials including but not limited to corn stover, corn husks, corn cobs, corn fiber, wheat straw, milo stubble, switchgrass, deciduous wood, coniferous wood, deciduous or coniferous wood chips, deciduous or coniferous sawdust, citrus waste, urban green waste, hay, straw, rice straw, sugarcane, sugarcane bagasse, grain cleanings, spent brewer's grain including dried distiller's grain (DDG) and dried distiller's grain with solubless (DDGS), rice hulls, barley straw, *salix*, spruce, poplar, eucalyptus, *Brassica carinata* residue, *Antigonum leptopus*, sweetgum, *Miscanthus, Sericea lespedeza*, Chinese tallow, hemp, rapeseed, *Sorghum bicolor*, soybean leaves, soybeans stems, soybean pods, soybean residue, sunflower leaves, sunflower stems, seedless sunflower heads, sunflower hulls, sunflower residue, Arundo, nut shells, deciduous leaves, cotton fiber, manure, coastal Bermuda grass, clover, Johnsongrass, flax, buckwheat straw, oat straw, millet straw, amaranth straw, amaranth stems, amaranth leaves, amaranth residue, spelt straw, rye straw, alfalfa, and bamboo.

Lignocellulose-degrading compositions of the invention are produced on a variety of feedstocks and nutrient preparations as described herein. Solid state fermentation systems are adapted to use different feedstocks allowing customized lignocellulose-degrading compositions for the specific substrates used in saccharification and fermentation steps.

A variety of fungal strains have been adapted to the production of lignocellulose-degrading compositions in solid state fermentation systems. Different strains of fungi provide different lignocellulose-degrading compositions and are applied in the compositions and methods of the invention to improve ethanol yield.

In some embodiments, lignocellulose-degrading compositions (e.g., generated via the solid state fermentation processes described herein) are utilized independently for conversion of fibrous plant materials to fermentable sugars. In some embodiments, lignocellulose-degrading compositions (e.g., generated via the solid state fermentation processes described herein) are utilized together with other lignocellulose-degrading agents and/or other active agents such as buffers, nutrient media, surfactants (including but not limited to TWEEN-20, TWEEN-80, polyoxyethylene glycol, TWEEN-81, Emulgen 147, amphoteric anhitole 20BS, cationinc Q-86W, sophorolipid, rhamnolipid, and bacitracin), salts, antibiotics (including but not limited to LACTOSIDE antibiotic (Ethanol Technology, Milwaukee, Wis.)), minerals, osmolytically active agents, purified or crude enzymes, nitrogen sources, and/or carbon sources.

In some embodiments, the present invention provides a method of ethanol fermentation that utilizes the activities of at least one active ethanologenic microbe. In experiments conducted during development of embodiments of the present invention, *Saccharomyces cerevisiae* was used to convert fermentable sugars in corn/corn cob mash to ethanol. Other yeast strains or species described herein are equally useful in this process and may allow increased ethanol production efficiencies.

Beyond producing enzymes to metabolize a particular substrate, fungi also have the ability to alter the nutritional characteristics of the materials on which they grow. Thus, in some embodiments, compositions and methods of the present invention find use in the animal feed industry. For example, compositions and methods produced by SSF of lignocellulosic feedstock described herein provide foodstuffs (e.g., food additives and/or supplements) for agricultural food and feed applications (e.g., to meet the nutritional requirements of livestock more efficiently).

EXPERIMENTAL

The following examples are provided in order to demonstrate and further illustrate certain embodiments and aspects of the present invention and are not to be construed as limiting the scope thereof.

Example 1

Solid-state Fermentation Products Grown on Dried Distillers Grains with Solubles (DGGS) Substrate Materials and Methods Organisms: Strains of *Aspergillus oryzae* and *Rhizopus oligosporus* were used for solid-state fermentation. Both strains are designated as Generally Regarded As Safe (GRAS) organisms. Strains were stored on Difco Potato Dextrose Agar slopes at 4° C. until required.

Two yeast strains used for the fermentation of the corn mashes were commercially available strains of *Saccharomyces cerevisiae*. SUPERSTART (Ethanol Technology, Milwaukee, Wis., USA) was an active dry yeast (ADY) preparation with a cell count of $20\times10^9$ cells/g at 85% viability and THERMOSACC (Ethanol Technology, Milwaukee, Wis., USA) was a wet cake preparation with a cell count of $15\times10^9$/g at 90% viability.

Yeast addition to the corn mash fermentation: Yeast was added to the mash to give a final concentration of $30\times10^6$ live yeast cells/g of mash.

Source of DDGS: DDGS was provided by two commercial companies. Canadian Mist (Collingwood Ontario, Canada) provided DDGS from a whisky production process and Commonwealth Agri-Energy (Hopkinsville, Ky., USA) provided DDGS from a fuel ethanol production process. Canadian Mist uses a combination of corn and barley malt for their fermentation process. Commonwealth Agri-Energy uses 100% yellow #2 corn.

Preparation of Seed Fungal Culture: Media for Fungal Propagation Contained the following: corn starch (6.0% w/v) (PulpTex 12608, Cargill, Cedar Rapids, Iowa); BACTO peptone (1.8% w/v) (Difco); dextrose (0.50% w/v); yeast extract (0.50% w/v) (LP0021, Oxoid, Ltd., Basingstoke, Hampshire, England); $MgSO_4.7H_2O$ (0.15% w/v); KCl (0.10% w/v); $KH_2PO_4$ (0.10% w/v); de-ionized $H_2O$. Components were heated in 500 mL Erlenmeyer flasks until the starch gelatinized.

The contents of a stock PDA slope containing the fungal culture were used to inoculate the cooled media and the flasks were incubated with shaking at 200 rpm for 72 h at 30° C.

From this liquid seed culture, a 1:4 dilution in sterile de-ionized water was made and employed as the inoculum for the DDGS.

Preparation and Fermentation of DDGS: Erlenmeyer flasks (500 mL) containing 10 g of DDGS were autoclaved at 105° C. for 30 min and cooled to room temperature. Each flask was inoculated with 4 mL and 6 mL of the liquid inoculum from the liquid seed cultures of *Aspergillus oryzae* and *Rhizopus oligosporus* respectively, mixed thoroughly, and placed in an incubator at 30° C. and 90% relative humidity for a maximum of 120 h.

Laboratory Preservation of DDGS product: Although the DDGS fermented product can be used as a wet addition to the corn mash fermentation, for consistency between experimental trials and ease of long term laboratory storage, flask contents were freeze dried (Freezemobile 25 ES, VirTis, SP Industries, Inc., Gardiner, N.Y., USA).

Corn Mash Preparation: The substrate for the fermentations was a liquefied corn mash containing 30% (w/v) dissolved solids. To maintain consistency, a large quantity of commercial corn was purchased, divided into 10 kg batches, sealed in air tight foil bags and stored in boxes at room temperature until needed. Prior to the start of fermentation, the corn was ground using a hammer mill fitted with a #4 screen (1.588 mm mesh openings).

To prepare the mash, ground corn was slowly added to water and heated to 60° C. The slurry was continuously mixed during the cooking phase using a homogenizer (Silverson Machines, Inc., East Longmeadow, Mass., USA). Following the addition of the corn, α-amylase (SPEZYME XTRA, Genencor, Rochester, N.Y., USA) (0.06% by weight of solids) was added to reduce viscosity and prevent starch retrogradation. The slurry was heated to 85° C. and held at this temperature for 20 min before autoclaving at 121° C. for 20 min. After autoclaving, the mash was cooled to 85° C. and the remaining α-amylase (0.04% by weight of solids) was added. The mash was maintained at this temperature for 1 h with constant stirring, and then allowed to cool to 30° C. Water lost during autoclaving was replaced with sterile water. The antibiotic product LACTOSIDE (Ethanol Technology, Milwaukee, Wis., USA) was added (5 μg/mL) to control bacterial growth and to ensure consistency between experiments. Urea (Ulrich Chemical, Galveston, Tex.) at 0.016% (w/w) was added as an additional nitrogen source. Glucoamylase (Distillase L-400 Genencor International, Rochester, N.Y.) (0.06% by weight of solids) was added to saccharify the corn mash substrate.

Erlenmeyer flasks (500 mL scale) containing 200 g of mash were prepared in triplicate for the fermentation with SUPERSTART yeast and the addition of SSF products produced with *Aspergillus oryzae* on DDGS sourced from either a whisky or a fuel ethanol facility.

Bellco jars (4 L scale) containing 1000 g of mash were prepared in duplicate for two fermentation trials with THERMOSACC yeast and additions of SSF products produced with *Aspergillus oryzae* and *Rhizopus oligosporus* on DDGS sourced from a fuel ethanol facility. THERMOSACC yeast has been reported to be a more heat tolerant strain (See, e.g., Graves, Yeast and corn mash fermentation, Ph.D. Thesis, Heriot-Watt University, Scotland, 2007; herein incorporated by reference).

Standardization of freeze dried product for protease activity. The dried SSF products were analyzed for protease activity using the standard HUT method (See, e.g., Food Chemicals Codex, 4$^{th}$ ed., 1996, National Academy Press, Washington, D.C., pp. 812-813; herein incorporated by reference) at pH 4.7.

Figure 2:
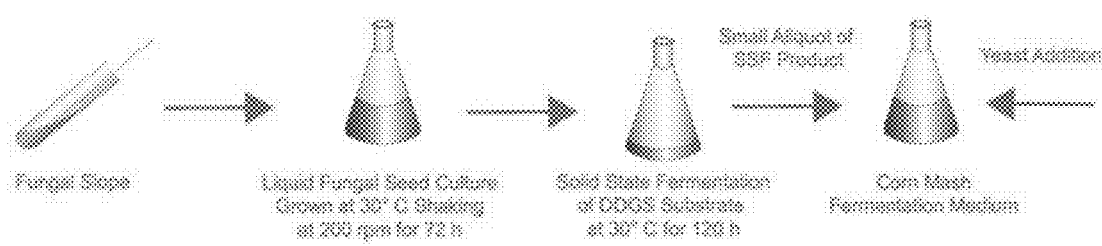
FIG. 2 shows process flow from seed culture inoculation to corn mash fermentation inoculation in an embodiment of the present invention.

Addition of SSF product to corn mash fermentations: Freeze dried SSF product addition was added based on equivalent protease activity. SSF product from *Aspergillus oryzae* produced using DDGS from a whisky source was added at 0.01% (w/w) and at 0.02% (w/w) from the SSF product produced using DDGS from a fuel ethanol source. SSF product from *Rhizopus oligosporus* produced using DDGS from a fuel ethanol source was added at 0.07% (w/w). FIG. 2 illustrates the laboratory scale up process flow.

Sampling of the corn mash and HPLC analysis: Fermentation samples (8 mL) were analyzed for carbohydrates (dextrin, maltotriose, maltose and glucose), ethanol, and lactic acid and acetic acid by high-performance liquid chromatography (HPLC). The samples collected were centrifuged (4000 rpm for 15 min), and the supernatant was appropriately diluted and filtered (0.20 µm filter) prior to analysis. A sample or standard solution (20 µL) was injected onto a Bio-Rad HPX-87H Aminex ion exclusion column coupled to a refractive index detector (Waters Chromatographic Division, Milford, Mass.). The column was operated at 65° C. and sulfuric acid (2 mM) was used as the mobile phase at a flow rate of 0.6 mL/min. The data were processed by Millennium Software (Waters Chromatographic Division).

Figure 3:
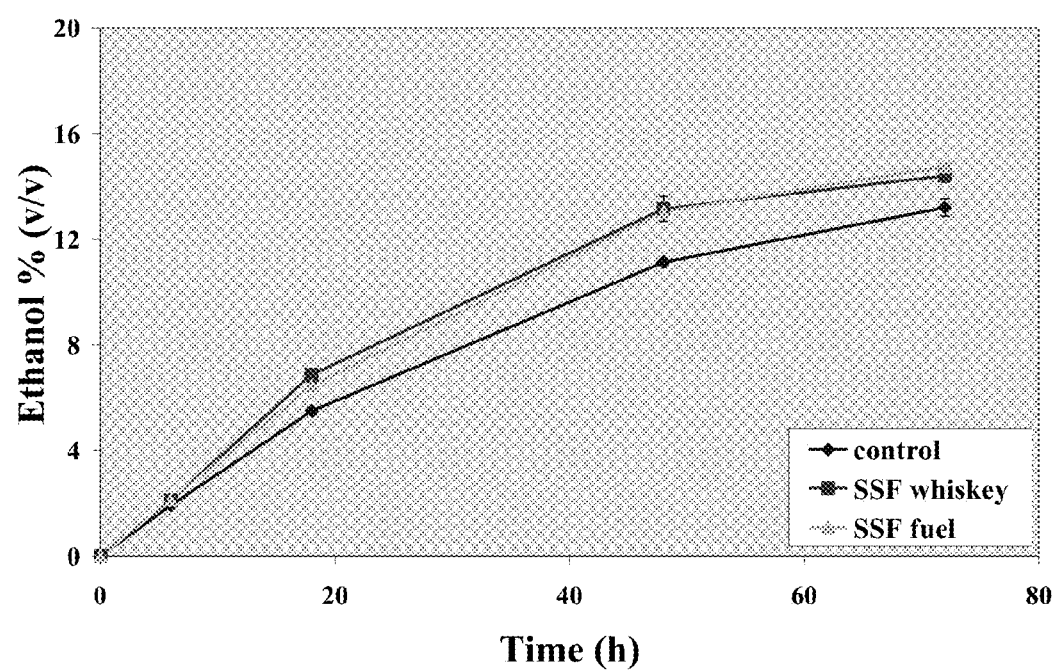
FIG. 3 shows ethanol generation using compositions produced in an embodiment of the present invention. Ethanol production was quantified during the course of a standard corn mash fermentation (500 ml Erlenmeyer flasks) using SUPERSTART yeast at 30° C. supplemented with the solid-state fermentation (SSF) enzyme product of *A. oryzae* grown on dried distiller's grain with solubles (DDGS) from either a whiskey or fuel ethanol source. Control (diamonds), whiskey SSF product (squares), fuel ethanol SSF product (triangles).

Results: The addition of the SSF product resulted in a significant increase in ethanol yield at 72 h (P<0.001) compared to the control, in which no SSF product was added. The maximum ethanol produced after 72 h using the shake flasks with the whiskey DDGS enzyme product was 14.41% (v/v) and with the DDGS fuel enzyme product, it was 14.75% (v/v). The control showed a maximum of 13.20% (v/v) at 72 h. FIG. 3 illustrates that there was not a large difference when fermented DDGS from a whiskey distillery was used, compared to DDGS from a fuel ethanol source. Improved ethanol yields, expressed as a percentage of the control, were 11.7% and 9.2% respectively.

that the addition of the antibiotic product LACTOSIDE (Ethanol Technology, Milwaukee, Wis., USA) was effective in controlling bacterial growth in order to ensure consistency between experiments. Glycerol levels were in normal range for this type of fermentation (See, e.g., Russell, Understanding yeast fundamentals, In: The Alcohol Textbook, Jacques et al., eds., Nottingham University Press, Nottingham, UK, pp. 85-119; herein incorporated by reference in its entirety).

TABLE 1

Acetic acid, lactic acid, and glycerol levels in a corn mash fermentation (shake flasks) conducted using SUPERSTART yeast and additions of SSF enzyme complex produced from DDGS (fuel ethanol plant or whiskey distillery)

| Acetic Acid % (w/v) | 6 h | 18 h | 48 h | 72 h |
|---|---|---|---|---|
| Control | <0.01 | 0.04 | 0.02 | <0.01 |
| Fuel DDGS Product | <0.01 | 0.04 | 0.02 | 0.02 |
| Whiskey DDGS Product | <0.01 | 0.03 | 0.02 | <0.01 |
| Lactic Acid % (w/v) | 6 h | 24 h | 48 h | 65 h |
| Control | <0.01 | 0.04 | 0.02 | 0.01 |
| Fuel DDGS Product | <0.01 | 0.04 | 0.02 | 0.02 |
| Whiskey DDGS Product | <0.01 | 0.03 | 0.02 | 0.01 |
| Glycerol % (w/v) | 6 h | 24 h | 48 h | 65 h |
| Control | 0.31 | 0.67 | 0.75 | 0.78 |
| Fuel DDGS Product | 0.30 | 0.63 | 0.68 | 0.71 |
| Whiskey DDGS Product | 0.31 | 0.63 | 0.66 | 0.72 |

Examining residual glucose over the fermentation period (See Table 2), it was observed that in the control fermentation, even at 72 h, there was still glucose available for fermentation, at a level of 2.05% (w/v). This was consistent with the lower ethanol seen in the control at 72 h compared to the flasks with DDGS product addition.

TABLE 2

Residual glucose % (w/v) and ethanol production % (v/v) in a corn mash fermentation (shake flasks) conducted using SUPERSTART yeast and additions of SSF enzyme complex produced from DDGS (fuel ethanol plant or whiskey distillery)

| Fermentation Flask (500 ml) | Glucose % (w/v) at 0 h | Residual Glucose % (w/v) at 6 h | Residual Glucose % (w/v) at 18 h | Residual Glucose % (w/v) at 48 h | Residual Glucose % (w/v) at 72 h | Ethanol % (v/v) at 72 h |
|---|---|---|---|---|---|---|
| Control | 1.11 | 2.56 | 4.2 | 2.98 | 2.05 | 13.20 |
| Fuel DDGS Product | 1.11 | 3.68 | 3.95 | 2.14 | 0.84 | 14.75 |
| Whiskey DDGS Product | 1.11 | 3.12 | 3.67 | 1.87 | 0.84 | 14.41 |

HPLC analyses of the fermentation for acetic acid, lactic acid, and glycerol levels are shown in Table 1. Lactic acid and acetic acid levels were low, confirming that the fermentations were not contaminated with bacteria. The fermentations also underwent microscopic analysis. These observations provide There was little residual maltose present by 48 h (See Table 3) and the increase in maltose from 6 h to 18 h indicates that the hydrolysis to glucose and maltose of the larger starch molecules, as well as compounds such as maltotetraose and maltotriose, was still occurring.

TABLE 3

Residual maltose % (w/v) and ethanol production % (v/v) in a corn mash fermentation (shake flasks) conducted using SUPERSTART yeast and additions of SSF enzyme complex produced from DDGS (fuel ethanol plant or whiskey distillery)

| Fermentation Flask (500 ml) | Maltose % (w/v) at 0 h | Residual Maltose % (w/v) at 6 h | Residual Maltose % (w/v) at 18 h | Residual Maltose % (w/v) at 48 h | Residual Maltose % (w/v) at 72 h | Ethanol % (v/v) at 72 h |
|---|---|---|---|---|---|---|
| Control | 1.60 | 3.32 | 6.25 | 0.93 | 0.63 | 13.20 |
| Fuel DDGS Product | 1.60 | 3.96 | 5.16 | 0.55 | 0.64 | 14.75 |
| Whiskey DDGS Product | 1.60 | 3.73 | 5.18 | 0.54 | 0.62 | 14.41 |

At 6 h the maltotriose was still accumulating in the mash, due to the action of the various enzymes added to the mash, but by 18 h the amount of maltotriose present was less than 1% (Table 4).

TABLE 4

Residual maltotriose % (w/v) and ethanol production % (v/v) in a corn mash fermentation (shake flasks) conducted using SUPERSTART yeast and additions of SSF enzyme complex produced from DDGS (fuel ethanol plant or whiskey distillery)

| Fermentation Flask (500 ml) | Maltotriose % (w/v) at 0 h | Residual Maltotriose % (w/v) at 6 h | Residual Maltotriose % (w/v) at 18 h | Residual Maltotriose % (w/v) at 48 h | Residual Maltotriose % (w/v) at 72 h | Ethanol % (v/v) at 72 h |
|---|---|---|---|---|---|---|
| Control | 2.5 | 4.32 | 0.94 | 0.29 | 0.23 | 13.20 |
| Fuel DDGS Product | 2.5 | 4.01 | 0.47 | 0.30 | 0.18 | 14.75 |
| Whiskey DDGS Product | 2.5 | 4.23 | 0.70 | 0.25 | 0.15 | 14.41 |

While the present invention is not limited to any particular mechanism, and an understanding of the mechanism is not necessary to practice the present invention, since the amount of maltose present at 18 h was still in the range of 5 to 6%, it was contemplated that rather than the yeast taking up the maltotriose, it was the action of the amylases in the mash hydrolysing the maltotriose to smaller units such as glucose and maltose, that was responsible for most of the disappearance of this sugar from the mash. By 48 h the maltotriose was less than 0.3% (w/v).

The thick viscosity of the mash hindered consistent and accurate measurement of the quantity of dextrins present in the mash prior to yeast inoculation. At 6 h the mash was not as viscous and reproducible dextrin numbers could be obtained. Table 5 provides that the fermentations with the added SSF enzyme product contained less dextrin material at 6 h, and at 72 h there was still more dextrin material present in the control, indicating that the enzymes in the SSF product had released additional carbohydrates for the yeast to utilize.

TABLE 5

Residual dextrins % (w/v) and ethanol production % (v/v) in a corn mash fermentation (shake flasks) conducted using SUPERSTART yeast and additions of SSF enzyme complex produced from DDGS (fuel ethanol plant or whiskey distillery)

| Fermentation Flask (500 ml) | Dextrins % (w/v) at 0 h | Dextrins % (w/v) at 6 h | Dextrins % (w/v) at 18 h | Dextrins % (w/v) at 48 h | Dextrins % (w/v) at 72 h | Ethanol % (w/v) at 72 h |
|---|---|---|---|---|---|---|
| Control | 23.50 | 17.37 | 9.09 | 4.78 | 1.32 | 13.20 |
| Fuel DDGS Product | 23.50 | 15.57 | 8.67 | 2.86 | 0.81 | 14.75 |
| Whiskey DDGS Product | 23.50 | 16.13 | 9.04 | 3.11 | 0.83 | 14.41 |

Figure 4:
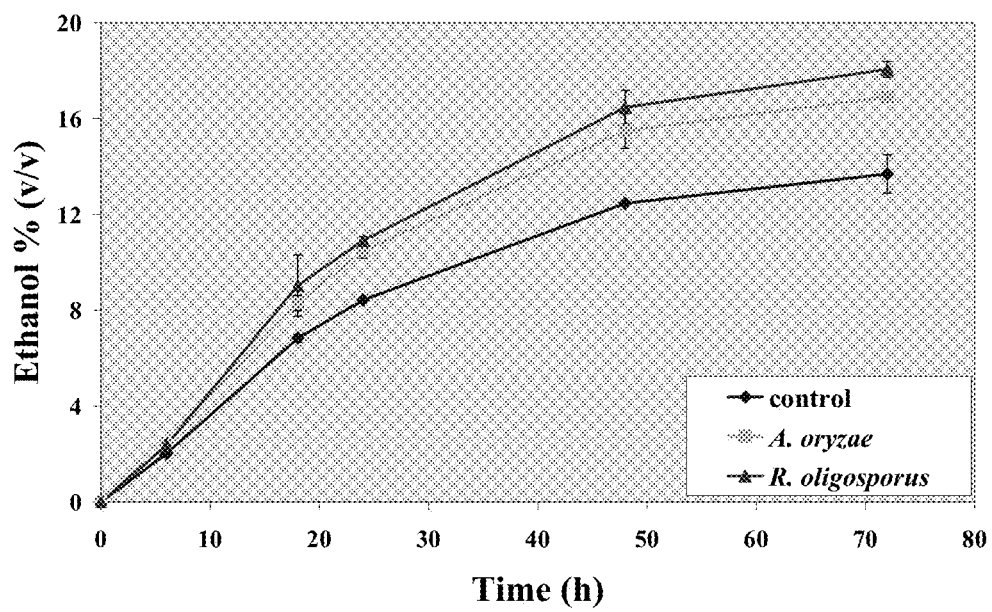
FIG. 4 shows ethanol generation using compositions produced in an embodiment of the present invention. Data are shown from two separate experiments (top and bottom panels). Ethanol production was quantified during the course of a standard corn mash fermentation (4 L Bellco fermentation vessels) using THERMOSACC yeast at 30° C. supplemented with solid-state fermentation (SSF) enzyme products of *A. oryzae* and *R. oligosporus* grown on dried distiller's grain with solubles (DDGS) (fuel ethanol plant). Control (diamonds), *A. oryzae* SSF product (squares), *R. oligosporus* SSF product (triangles).
Figure 4:
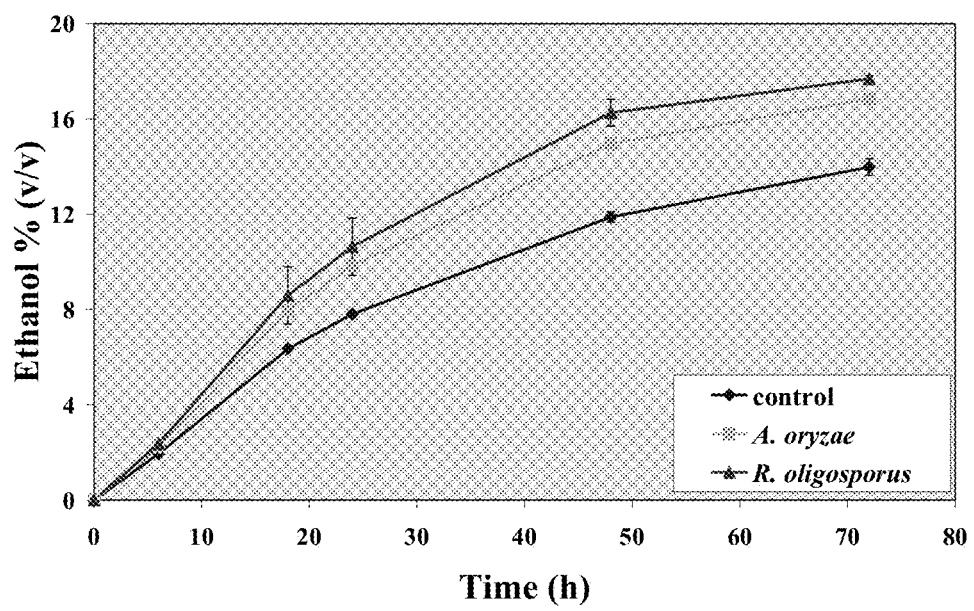

Experiments were carried out on a larger scale (4 L Bellco fermenters) and with THERMOSACC yeast. The effect of the SSF product addition in terms of ethanol production was even greater and the results repeatable over independent fermentations (See FIGS. 4A and 4B). FIGS. 4A and 4B show experiments conducted representing fermentations that were carried out at different times with freshly prepared corn mashes.

The highest ethanol values at 72 h were seen with the *R. oligosporus* product additions with 17.68% (v/v) and 18.06% (v/v), from first and second trials, respectively. The *A. oryzae* product additions gave ethanol yields of 16.84% (v/v) and 16.90% (v/v) for the first and second trials, respectively. The control fermentations contained 13.98% (v/v) and 13.69% (v/v) ethanol for both the first and second trial, respectively. The results were statistically significant between the control and the fermentations with the SSF product additions (P=0.001 and P=0.007) for both trials. FIG. 4A illustrates a 26.46% and 20.45% ethanol increase over the control for the two treatments and FIG. 4B illustrates ethanol increases of 31.92% and 23.44% compared to the control.

HPLC analyses of corn mash fermentations were also carried out on the fermentations in the Bellco vessels. Although a different strain of yeast was used for these experiments, the patterns were very similar to what was observed in the shake flasks described above in terms of sugar hydrolysis and sugar uptake by the yeast. Tables 6-9 show residual glucose, maltose, maltotriose and dextrins for the first trial. As before, LACTOSIDE was added to the fermentations, and once again very low lactic acid and acetic acid values indicated minimal contamination.

TABLE 6

Residual glucose % (w/v) and ethanol production % (v/v) in a corn mash fermentation (Bellco vessels) conducted using THERMOSACC yeast and additions of SSF enzyme complex produced from either *A. oryzae* or *R. oligosporus* on DDGS (fuel ethanol plant)

| Fermentation (Bellco Vessel) | Residual Glucose % (w/v) at 6 h | Residual Glucose % (w/v) at 18 h | Residual Glucose % (w/v) at 24 h | Residual Glucose % (w/v) at 48 h | Residual Glucose % (w/v) at 72 h | Ethanol % (v/v) at 72 h |
|---|---|---|---|---|---|---|
| Control | 4.11 | 4.43 | 5.22 | 5.98 | 5.05 | 13.98 |
| *A. oryzae* DDGS Product | 4.15 | 2.27 | 2.41 | 2.24 | 1.42 | 16.84 |
| *R. oligosporus* DDGS product | 4.50 | 2.30 | 2.54 | 1.13 | 0.21 | 17.68 |

TABLE 7

Residual maltose % (w/v) and ethanol production % (v/v) in a corn mash fermentation (Bellco vessels) conducted using THERMOSACC yeast and additions of SSF enzyme complex produced from either *A. oryzae* or *R. oligosporus* on DDGS (fuel ethanol plant)

| Fermentation (Bellco Vessel) | Residual Maltose % (W/V) at 6 h | Residual Maltose % (w/v) at 18 h | Residual Maltose % (w/v) at 24 h | Residual Maltose % (w/v) at 48 h | Residual Maltose % (w/v) at 72 h | Ethanol % (v/v) at 72 h |
|---|---|---|---|---|---|---|
| Control | 5.27 | 8.11 | 5.34 | 0.51 | 0.51 | 13.98 |
| *A. oryzae* DDGS Product | 5.68 | 7.90 | 5.01 | 0.45 | 0.53 | 16.84 |
| *R. oligosporus* DDGS product | 6.09 | 6.75 | 3.47 | 0.52 | 0.55 | 17.68 |

TABLE 8

Residual maltotriose % (w/v) and ethanol production % (v/v) in a corn mash fermentation (Bellco vessels) conducted using THERMOSACC yeast and additions of SSF enzyme complex produced from either *A. oryzae* or *R. oligosporus* on DDGS (fuel ethanol plant)

| Fermentation (Bellco Vessel) | Residual Maltroise % (w/v) at 6 h | Residual Maltotroise % (w/v) at 18 h | Residual Maltotroise % (w/v) at 24 h | Residual Maltotroise % (w/v) at 48 h | Residual Maltotroise % (w/v) at 72 h | Ethanol % (v/v) at 72 h |
|---|---|---|---|---|---|---|
| Control | 5.21 | 0.37 | 0.25 | 0.39 | 0.18 | 13.98 |
| *A. oryzae* DDGS product | 5.17 | 0.23 | 0.29 | 0.41 | 0.12 | 16.84 |
| *R. oligosporus* DDGS product | 4.82 | 0.33 | 0.36 | 0.39 | 0.12 | 17.68 |

TABLE 9

Residual dextrins % (w/v) and ethanol production % (v/v) in a corn mash fermentation (Bellco vessels) conducted using THERMOSACC yeast and additions of SSF enzyme complex produced from either *A. oryzae* or *R. oligosporus* on DDGS (fuel ethanol plant)

| Fermentation (Bellco Vessel) | Residual Dextrins % (w/v) at 6 h | Residual Dextrins % (w/v) at 18 h | Residual Dextrins % (w/v) at 24 h | Residual Dextrins % (w/v) at 48 h | Residual Dextrins % (w/v) at 72 h | Ethanol % (v/v) at 72 h |
|---|---|---|---|---|---|---|
| Control | 14.83 | 8.08 | 7.08 | 3.23 | 0.76 | 13.98 |
| *A. oryzae* DDGS product | 13.97 | 8.05 | 6.98 | 2.38 | 0.51 | 16.84 |
| *R. oligosporus* DDGS product | 13.30 | 7.79 | 6.55 | 1.52 | 0.51 | 17.68 |

Because corn contains a relatively low level of total free amino nitrogen (FAN), in some embodiments, fermentations to produce ethanol were supplemented with a nitrogen source such as urea or ammonium sulfate to optimize the process (See, e.g., Russell, Understanding yeast fundamentals, In: The Alcohol Textbook, Jacques et al., eds., Nottingham University Press, Nottingham, UK, pp. 85-119; herein incorporated by reference in its entirety). Addition of urea is usually limited to non-beverage applications due to concerns with urethane formation. Urethane, a potential carcinogen, forms when urea reacts with ethanol.

In some embodiments, another method of providing additional nitrogen to the yeast, in the form of amino nitrogen, was through the addition of proteases to the fermentation system. Proteases increase the hydrolysis of the proteins present in the corn mash. Proteolytic enzymes have been shown to improve ethanol yield in the dry grind process (See, e.g., Lantero et al., 1993, U.S. Pat. No. 5,231,017), in the E-Mill process (Singh et al., 2005, Cereal Chem., 82, 187-190), and also to increase the amount of FAN in a maize hydrolyzate (Perez-Carrillo et al, 2007, Cereal Chem., 84, 607-613).

The structural complexity of the nitrogen source has an effect on yeast growth and ethanol yield. A more complex nitrogen source, such as peptone, has demonstrated higher biomass accumulation and ethanol production when compared to ammonium sulfate (See, e.g., de Cruz et al., 2002, J Instit. Brewing, 108, 54-61).

The optimal inclusion rate of supplemental nitrogen sources or proteolytic enzymes depends on many factors such as the particular yeast strain and the economics of the return on the investment of particular levels of supplementation. For the fermentations described herein, the inclusion rate of 0.016% (w/w) urea, an average level used by a number of fuel ethanol plants in North America, is considerably lower than the maximum level discussed by Jones and Ingledew (See, e.g., Jones et al., 1994, Process Biochem., 25, 483-488). Therefore, while the present invention is not limited to any particular mechanism of action, and an understanding of the mechanism is not necessary to practice the present invention, the present invention provides that the observed response with the addition of the SSF product, containing protease enzyme activity, is attributed, in part, to increasing the amount of amino nitrogen available during fermentation. Further digestion of the protein fraction of corn also liberates additional fermentable sugars bound to proteins that would be otherwise unavailable to the yeast.

While protease was the primary enzyme of interest for this particular set of studies, one of the major advantages of an SSF product addition is that the enzymatic product contains a large number of different enzymes (e.g., those described herein) with activities that work in combination to break down a given substrate (e.g. cellulases) to make additional sugars available to the yeast. Thus, in some embodiments, the present invention provides that the further digestion of poly- and oligosaccharides into glucose and other fermentable sugars contributes to higher ethanol concentrations. In some embodiments, the presence of additional amylolytic and fibrolytic enzymes, even at low levels, contribute to the observed increase in ethanol production. Thus, the present invention provides that the addition of a SSF enzyme product adds considerable value to the fermentation by improving ethanol yield.

Example 2

Nutritional Improvement of Distillers Grains by Solid State Fermentation

Materials and Methods: Strains of *Rhizopus oligosporus* and *Aspergillus oryzae* were used for fermentations on DDGS. All the microorganisms that were employed are generally regarded as safe (GRAS) and suitable for animal feed applications. DDGS was obtained from a whisky distillery Canadian Mist (Collingwood, Ontario, Canada) and a DDGS fuel ethanol source (Commonwealth Agri-Energy, Hopkinsville, Ky., USA). Canadian Mist used a proprietary blend of corn and barley malt for their fermentation process. Commonwealth Agri-Energy used 100% yellow #2 corn.

Seed Culture and Inoculum Preparation: Media for fungal propagation contained the following: corn starch (6.0% w/v) (PulpTex 12608, Cargill, Cedar Rapids, Iowa); Bacto™ peptone (1.8% w/v) (Difco); dextrose (0.50% w/v); yeast extract (0.50% w/v) (LP0021, Oxoid, Ltd., Basingstoke, Hampshire, England); $MgSO_4 \cdot 7H_2O$ (0.15% w/v); KCl (0.10% w/v); $KH_2PO_4$ (0.10% w/v); de-ionised $H_2O$. Components were heated in 500 ml Erlenmeyer flasks until the starch gelatinized.

DDGS from the same source that was used for solid-state fermentation (2.0% w/v) was added and the flasks were autoclaved at 121° C. for 20 min.

The contents of a stock PDA slope containing the applicable fungal culture were used to inoculate the cooled media and the flasks were incubated with shaking at 200 rpm for 72 h at 30° C.

From this liquid seed culture a 1:4 dilution in sterile de-ionized water was used as inoculum.

Fermentation: Erlenmeyer flasks (500 mL) containing 20 g of DDGS were autoclaved at 105° C. for 30 min and cooled to room temperature. Each flask was inoculated with 4 mL and 6 mL of the liquid inoculum from the liquid seed cultures of

*Aspergillus oryzae* and *Rhizopus oligosporus* respectively and mixed thoroughly. Flasks corresponding to Time 0 were set aside while the remaining flasks were placed in an incubator at 30° C. and 90% relative humidity for a maximum of 120 h.

Laboratory Preservation of DDGS Product: For consistency in laboratory storage, until analysis could be completed, the contents of all flasks were freeze dried (Freezemobile 25 ES, VirTis, SP Industries, Inc., Gardiner, N.Y., USA).

Analysis

Dry matter mass: The samples from before and after fermentation were weighed after freeze drying, and the moisture levels in the samples were determined using a moisture analyzer (Denver Instruments IR-200, Denver, Colo., USA). Dry matter mass for samples before fermentation (Time 0) was designated as 100%, and this was used as the basis for comparison. All analyses are reported on a dry matter basis.

Samples before and after fermentation were sent to Midwest Laboratories, Inc. (Omaha, Nebr.) for proximate analysis (crude protein, neutral detergent fiber (NDF), acid detergent fiber (ADF), ash, and fat analysis).

Figure 5:
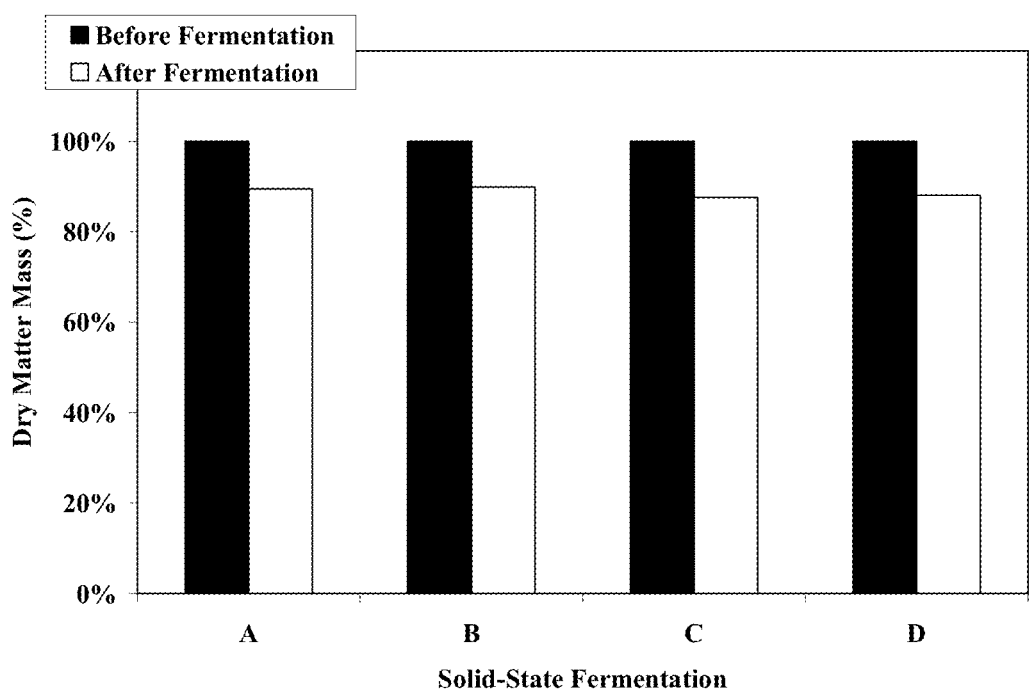
FIG. 5 shows changes in mass of dry matter before and after solid-state fermentation using compositions of an embodiment of the present invention. A, *Rhizopus* grown on whisky distillers DDGS; B, *Rhizopus* grown on fuel ethanol DDGS; C, *Aspergillus* grown on whisky distillers DDGS; D, *Aspergillus* grown on fuel ethanol DDGS.

Results: Observations during the fermentations and the analytical results indicate that DDGS is a viable substrate for solid-state fermentation. Visually, the microorganism covered the DDGS with white mycelia which formed a dense fungal mat throughout the substrate. Analytically, it was apparent that the organism metabolized the substrate by the disappearance of dry matter. Dry matter mass disappearance for the fermentations is presented in FIG. 5.

While considerable biomass was present after fermentation, direct determination of biomass in solid-state fermentation is very difficult, due to problems with separation of the microorganism from the substrate (See, e.g., Mitchell, 1992, Biomass determination in solid-state cultivation, In: Solid Substrate Cultivation, Mitchell et al., eds., Elsevier Applied Science, London, UK, pp. 53-63; herein incorporated by reference). Therefore, to gain a better understanding of what is happening during fermentation, proximate analysis, routinely used to characterize animal feed, was conducted before and after fermentation.

The changes in the nutrient profiles of the DDGS are notable, particularly with respect to crude protein, as it is one of the most expensive nutrients in animal diets (See, e.g., Belyea et al., 2004, Bioresource Tech., 94, 293-298). Crude protein is an estimate of the total protein content of a feed used by the feed industry and regulators. It includes true protein containing amino acids as well as non-protein nitrogen. Therefore, it does not provide information regarding the quality or availability of protein in a feed sample. The increase in crude protein for all fermentations, 16.0%, 12.6%, 17.4%, and 13.2% respectively as indicated in Table 10 is attributed to the disappearance of dry matter.

TABLE 10

Proximate analysis results and concentrated values (A) *Rhizopus* grown on whisky distillers DDGS (B) *Rhizopus* grown on fuel ethanol DDGS (C) *Aspergillus* grown on whisky distillers DDGS (D) *Aspergillus* grown on fuel ethanol DDGS

|  | Before Fermentation | After Fermentation | % Increase or Decrease | Theoretical Concentrated Value | Δ from Actual |
|---|---|---|---|---|---|
| A *Rhizopus* grown on whisky DDGS | | | | | |
| Crude Protein | 31.4% | 36.4% | 16.0% | 35.1% | 1.3% |
| NDF | 46.1% | 39.5% | −14.3% | 51.5% | −12.0% |
| ADF | 17.8% | 16.7% | −6.2% | 19.9% | −3.2% |
| Fat | 12.2% | 7.0% | −42.6% | 13.6% | −6.6% |
| B *Rhizopus* grown on fuel ethanol DDGS | | | | | |
| Crude Protein | 29.4% | 33.1% | 12.6% | 32.3% | 0.8% |
| NDF | 36.9% | 35.8% | −3.0% | 41.0% | −5.2% |
| ADF | 14.4% | 12.7% | −11.8% | 16.0% | −3.3% |
| Fat | 11.8% | 6.9% | −41.5% | 13.1% | −6.2% |
| C *Aspergillus* grown on whisky DDGS | | | | | |
| Crude Protein | 29.8% | 35.0% | 17.4% | 34.0% | 1.0% |
| NDF | 45.2% | 45.3% | 0.2% | 51.6% | −6.3% |
| ADF | 16.8% | 20.1% | 19.6% | 19.2% | 0.9% |
| Fat | 12.7% | 7.9% | −38.0% | 14.5% | −6.7% |
| D *Aspergillus* grown on fuel ethanol DDGS | | | | | |
| Crude Protein | 27.3% | 30.9% | 13.2% | 31.0% | −0.1% |
| NDF | 34.1% | 34.0% | −0.1% | 38.7% | −4.7% |
| ADF | 13.9% | 15.2% | 9.4% | 15.8% | −0.6% |
| Fat | 12.3% | 7.1% | −42.5% | 14.0% | −6.9% |

Figure 6:
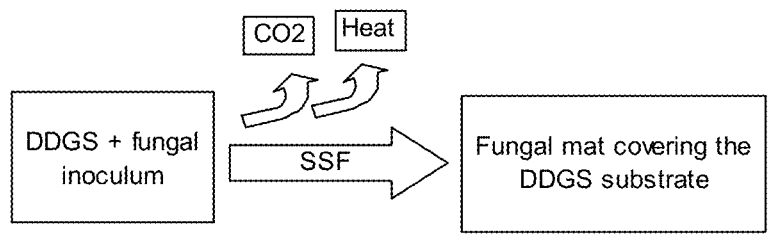
FIG. 6 shows a flowchart of solid-state fermentation in an embodiment of the present invention.

Ash analysis on the samples before and after solid-state fermentation indicated in no changes in the amount of ash present observed. The only losses during fermentation were heat and $CO_2$ (See FIG. 6).

This trend, however, was not observed for all nutritional values. The changes in the nutritional profile provide insight into the ability of the fungus to metabolise components in the DDGS. Saprophytic filamentous fungi require carbon and nitrogen for growth. The disappearance of carbon in the form of carbon dioxide is a result of the organism converting the accessible carbon sources into energy via the tricarboxylic acid (TCA) cycle. The primary carbon sources available to the microorganisms in DDGS, after the conversion of the fermentable sugars from corn into ethanol, are fat (triglycerides), cellulose, and hemicellulose.

Neutral detergent fiber (NDF) is an estimate of the plant cell wall components cellulose, hemicellulose, and lignin, while acid detergent fiber (ADF) estimates the plant cell wall portions only made up of cellulose and lignin. Hemicellulose comprises the difference in the two values.

Based on the disappearance of dry matter, it was possible to calculate concentrated values for each nutritional component. In other words, it was possible to calculate what the concentration of a particular nutritional component would have been based on the observed disappearance of material had it not been consumed. These values are listed Table 10.

Table 10 shows that the *Rhizopus* strain metabolized ~6% of the fat. In addition, the NDF and ADF values after fermentation were less than the theoretical increase due to dry matter disappearance, which provides that the organism utilized some of the hemicellulose and cellulose as it grew. The *Aspergillus* strain also metabolized a portion of the accessible fat (~5-6%) as well as some of the hemicellulose. The ADF value, however, was nearly the same as the concentrated value, indicating that the organism was unable to break down the cellulose or lignin portion of the distillers grains.

Traditionally, distiller's byproducts have been included as a nutrient source in ruminant diets due to their high fiber content (See, e.g., Ham et al., 1994, J Animal Sci., 72, 3246-3257; Singh et al., 2005, Cereal Chem., 82, 187-190). While the present invention is not limited to any particular mechanism, and an understanding of the mechanism is not necessary to practice the present invention, it is contemplated that microorganisms in the rumen assist the animal in breaking down cellulose and hemicellulose to form microbial protein, which is in turn utilized by the animal later in the digestion process. Much like the microorganisms present in the rumen, the ability of filamentous fungi to utilize hemicellulose and cellulose fractions is of interest since monogastric animals (poultry, swine, etc.) are unable to utilize these portions of the grain.

Fungi produce a wide spectrum of extracellular enzymes that can degrade polysaccharides, peptides, and fats into monomer units for protein synthesis and mycelial growth. When grown on DDGS, the enzymes expressed are specific to the substrate as the organisms produce what they need in order to grow with the nutrition available. Thus, in some embodiments, the present invention provides that ability to harvest an organisms' ability to break down such compounds and provides the opportunity for improved utilization of grain and agro-industrial residues such as spent grains for use as feed for monogastric animals.

Figure 7:
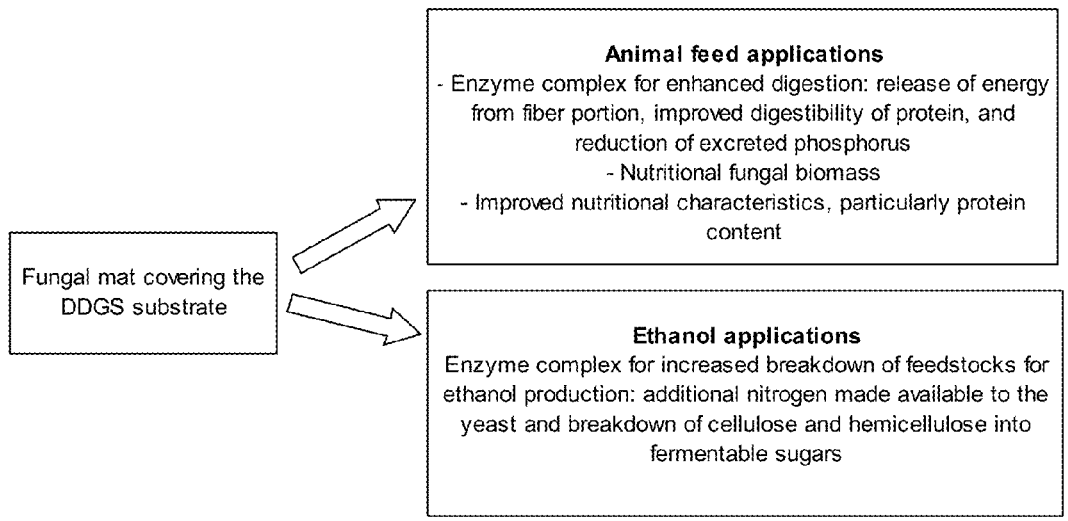
FIG. 7 shows applications for solid-state fermentation products (lignocellulose-degrading compositions) in some embodiments of the present invention.

Benefits of solid-state fermentation to the animal (See, e.g., FIG. 7) include improved nutritional characteristics of grain, particularly with respect to protein; nutritional fungal biomass; liberation of energy from the fiber portion of grain; improved protein digestibility; and increased phosphorus levels available to the animal, which reduces the amount of phosphorus excreted as waste.

While the present invention is not limited to any particular mechanism, and an understanding of the mechanism is not necessary to practice the present invention, it is contemplated that in a similar way to the fungi's ability to improve the digestibility of grain for monogastric animals, solid-state fermentation also increases the efficiency of yeast in converting grain into ethanol. Fungi are able to assist in breaking down feedstocks for ethanol production by releasing additional nitrogen available for the yeast and breaking down cellulose and hemicellulose into fermentable sugars.

Example 3

Production of Ethanol from Lignocellulosic Feedstock Using an Integrated Biorefinery Steps in a method for an integrated biorefinery producing ethanol from lignocellulosic feedstocks are depicted in FIG. 1 and are described herein.

A. Priming and Ethanologenic Feedstocks: Lignocellulosic priming feedstock was identified and characterized that supports the production of lignocellulose-degrading compositions and the ethanol fermentation process. Corncob was extensively used in experiments conducted during development of embodiments of the invention but other substrates such as switchgrass, wood chips and corn stover are contemplated to be utilizable with similar results. The lignocellulosic component of the ethanologenic feedstock mash produced for use in the ethanol co-fermentation process was 30% and the remaining 70% was made of ground corn kernels. Of the 30% lignocellulosic material (corncob), 25% was raw ground corncob and the other 5% was used to form a lignocellulose-degrading composition produced from solid state fermentation. The corncob (substantially free of kernels) was successively ground three times in a hammer mill with decreasing screen size to obtain a coarse, medium, and fine grind material. The corn grain and corncob ethanologenic feedstocks were ground separately and then mixed prior to an initial cooking step.

B. Solid State Fermentation and Production of Lignocellulose-degrading Compositions: The lignocellulose-degrading compositions were produced using a filamentous fungus (*Aspergillus niger*) grown on corncob in a Solid State Fermentation (SSF) process. The fermentation was initiated by mixing the ground corncob with 15% yeast extract and water, and then inoculating the mixture with a liquid fungal inoculum. This mixture of corncob and fungal inoculum was spread onto a stainless steel tray and allowed to grow for 5 days in a humidity-controlled (50%) chamber at 30° C. Subsequently, the "wet" lignocellulose-degrading composition that developed on the corncob was harvested for use in saccharification and fermentation steps.

C. The Cooking Process: The cooking process was carried out in a modified conventional distillery cooking system with adaptations to allow for the use of a more viscous mash. The addition of the lignocellulosic and starch-rich components of the ethanologenic feedstocks to the cook system occurred in steps to ensure a homogenous mixture that is processed into the fermenter. In the first step of the cooking process, the slurry containing a 28.5% solids mixture of ground corn (US #2, yellow dent, 12% moisture) and ground corncob (4-9% moisture) was mixed with water in a 150-L MicroFerm fermenter with overhead agitation (New Brunswick Scientific Co, Edison, N.J.). The success of this process was dependent on the appropriate addition of the ground corn and corncob to the water. Ground corn was added to the water with alpha-amylase (0.06% by weight of grain) and heated to 85° C. for 5 minutes. This initial slurry contained 21% solids. The corn was cooked initially without the cob to produce a thicker mash that allowed the corn cob to remain in suspension. The corn cob was added slowly to the ground corn mash and the cooking process continued at 85° C. for 20 minutes. The mash was agitated vigorously (350 rpm) using a SC3 blade (Chemineer, Cincinnati, Ohio) to maintain the ground cob in suspension while cooking. The mash was sterilized at 121° C. for 20 minutes and then cooled. Alpha-amylase (0.04% by wt. of grain) was added and the mash was cooked at 85° C. for an additional 60 minute period.

D. Saccharification of Lignocellulosic Feedstock: The saccharification process resulted in the degradation of lignocellulose to fermentable sugars. The lignocellulose-degrading composition was added slowly (5% of the grain) to the 70% corn/25% corncob mash. During this process, the mash was agitated vigorously (350 rpm) using the SC3 blade to maintain the cob in suspension and to prevent settling. The resulting mash contained 30% solids. The ideal ratio of ground corn to ground corncob in the final mash was 70/30. The wet lignocellulose-degrading compositions contributed 5% of total feedstock in the mash.

E. Ethanol Co-fermentation: The ethanol fermentation was characterized by simultaneous release of fermentable sugars from both corn starch and the lignocellulosic feedstock (corncob). Glucoamylase (0.06% by wt. of grain) was added to the mash to saccharify the starch substrate in the ground corn. Urea was added (1 g/L) as a nitrogen source. The mash was inoculated with 30 million cells/g of an active yeast culture (*Saccharomyces cerevisiae*). The ethanol fermentation was complete within approximately 48 h at 34° C. Traditional distillation and molecular sieve technologies were used to separate the ethanol and fermentation residuals.

Pilot plant studies focused on producing an effective lignocellulose-degrading compositions on corncob and evaluating the effects of the lignocellulose-degrading compositions on ethanol yields from feedstock mixtures containing ground corn (70%) and corncob (30%) in mash (30% dry solids) fed 0.1% urea and maintained at 34° C. The lignocellulose-degrading compositions were added as a wet fermented corn cob preparation to provide a final dry weight addition of 5% of the feedstock after the mash had been cooked and cooled to 34° C. An overall compilation of the process test data in 10 batch fermentations (150-L pilot fomenter) is provided in Table 11.

Feedstock fermentation in pilot plant fermenters receiving the lignocellulose-degrading compositions was also characterized by a decrease in the time required to reach maximum ethanol concentrations (24 hours vs 42 hours), greater protein content in the residuals (25% vs. 18%) and both lower neutral detergent fiber content (22% vs. 70%) and lower acid detergent fiber (10.2% vs. 19.6%) content in residuals. All observations were consistent with the net conversion of the lignocellulosic components in the corncob to ethanol at a rate of between 45 and 48 gallon per tonne of corncob.

TABLE 11

Effects of a specific solid-state enzyme complex on ethanol yields in pilot plant fermentations

| Parameter | Value |
|---|---|
| Concentration of ethanol (% v/v) in fermentations using ground corn as a feedstock (n = 6) | 14.9 ± 0.6 |
| Yield of ethanol (gal/tonne) in fermentation using ground corn as a feedstock (n = 6) | 119.4 ± 6.5 |
| Concentration of ethanol (% v/v) in fermentations using a mixture (70:30) of ground corn and corncob as a feedstock (n = 2) | 10.2 ± 0.5 |
| Yield of ethanol (gal/tonne) in fermentation using a mixture (70:30) of ground corn and corncob as a feedstock (n = 2) | 81.4 ± 4.2 |
| Estimate ethanol yield (gal/tonne) contributed from corncob in mixture in the absence of the enzyme | 0 |
| Concentration of ethanol (% v/v) in fermentations using a mixture (70:30) of ground corn and corncob as a feedstock with the addition (5%) of a solid-state enzyme complex (n = 2) | 12.1 ± 0.1 |
| Yield of ethanol (gal/tonne) in fermentation using a mixture (70:30) of ground corn and corncob as a feedstock with the addition (5%) of a solid-state enzyme complex (n = 2) | 97.1 ± 1.1 |
| Estimated ethanol yield (gal/tonne) contributed from corncob in the mixture with the addition of the solid-state enzyme complex | 13.5 |
| Calculated yield of ethanol from corncob (gal/tonne) entering integrated process with enzyme complex | 45.0 |

F. Quantification of Enzyme Activities in Lignocellulose-Degrading Compositions Lignocellulose-degrading compositions produced by solid-state fermentation were analyzed for moisture content, dry material content, ethanol content (initial and after 48 h fermentation), and enzyme activity (Table 12).

TABLE 12

Enzyme activities of lignocellulose-degrading compositions.

| SSF name | Sample # | % DM | CMCU/g | XU/g | BGU/g | HUT/g | CBU/g | Ethanol, % | 48 hr % glucose |
|---|---|---|---|---|---|---|---|---|---|
| 08-SSFCOB-18C+ | 1 | | | | | | | | 3.33 |
| 08-SSFDDGS20C+ | 2 | | | | | | | | 2.63 |
| 08-SSFST-21CobC+ | 3 | 59.3 | 78 | 805 | 408 | 217 | 61 | | 2.71 |
| 08-SSFCOB-22C+ | 4 | | | | | | | 1.67 | 3.64 |
| 08-SSFCOB-24C+ | 5 | 57.4 | 9 | 143 | 25 | 137 | 2 | 0.42 | 0.74 |
| 08-SSFCOB-25C+ | 6 | 49.7 | 72 | 778 | 378 | 165 | 84 | 1.52 | 2.51 |
| 08-SSFDBCOB-04C+ | 7 | 63.6 | 7 | 97 | 18 | 0 | 5 | 0.44 | 0.77 |
| 08-SSFST22COBC+ | 8 | 52.6 | 34 | 715 | 221 | 161 | 26 | 1.38 | 2.34 |
| 08-SSFCOB26C+ | 9 | 55.9 | 81 | 968 | 392 | 305 | 84 | 1.28 | 2.06 |
| 08SSFCOB27C+ | 10 | 56.3 | 59 | 531 | 348 | 268 | 33 | 1.80 | 3.56 |
| 08SSFSTCOB24C+ | 11 | 49.2 | 61 | 638 | 407 | 326 | 22 | 1.90 | 3.70 |
| 08SSFCOB28C+ | 12 | 49.8 | 76 | 886 | 558 | 609 | 35 | 1.91 | 3.71 |
| 08SSFST25COBC+ | 13 | 50.7 | 37 | 395 | 137 | 107 | 12 | 1.40 | 2.79 |
| 08SSF29COBC+ | 14 | 54.5 | 79 | 888 | 321 | 379 | 44 | 1.70 | 3.46 |
| 08SSFST26COBC+ | 15 | 53.0 | 35 | 326 | 162 | 142 | 15 | 1.04 | 2.06 |

TABLE 12-continued

Enzyme activities of lignocellulose-degrading compositions.

| SSF name | Sample # | % DM | CMCU/g | XU/g | BGU/g | HUT/g | CBU/g | Ethanol, % | 48 hr % glucose |
|---|---|---|---|---|---|---|---|---|---|
| 08SSFCOB30C+ | 16 | 53.1 | 102 | 1155 | 660 | 484 | 102 | 1.93 | 3.74 |
| 08SSFST27COBC+ | 17 | 52.1 | 69 | 788 | 385 | 220 | 28 | 1.68 | 3.41 |
| 08SSFCOB31C+ | 18 | 45.8 | 80 | 1159 | 423 | 321 | 71 | 1.96 | 3.99 |
| 08SSFST28COBC+ | 19 | 51.6 | 74 | | | 380 | 36 | 1.76 | 3.63 |
| 08SSF32COBC+ | 20 | 55.9 | 70 | | | | 58 | 1.50 | 2.97 |
| 1571 TF-7 Serdan | 21 | 95.2 | 74 | 142 | 255 | 220 | | 0.64 | 1.12 |
| 1577 TF-14 Serdan | 22 | 93.2 | 78 | 313 | 353 | 294 | | 0.92 | 1.96 |
| 1571 TF-6 Serdan | 23 | 86.3 | 70 | 160 | 265 | 107 | | 0.56 | 1.06 |
| 08SSF33COBC+ | 24 | 60.3 | 69 | | | 232 | 48 | 2.02 | 3.14 |
| 08SSFST29COBC+ | 25 | 53.4 | 62 | | | 244 | 27 | 1.70 | 2.59 |
| 08SSF34COBC+ | 26 | 54.0 | 72 | | | 285 | 46 | 2.13 | 3.93 |
| 08SSFST30COBC+ | 27 | 54.4 | 60 | | | 364 | 37 | 2.23 | 4.19 |
| 08SSF35COBC+ | 28 | 74.7 | 35 | | | 188 | 58 | 1.04 | 1.90 |
| 08SSFST31COBC+ | 29 | 55.2 | 50 | | | 260 | 20 | 1.03 | 2.13 |
| 08SSF36COBC+ | 30 | 57.6 | 66 | | | | | | |
| 08SSFST32COBC+ | 31 | 63.4 | 34 | | | 116 | | | |

% DM, percentage dry material; CMCU/g, cellulase determined as carboxymethylcellulase units per gram dry material; XU/g, xylanase determined as xylanase units per gram dry material; BGU/g, beta-glucanase units per gram dry material; HUT/g, protease units per gram dry material; CBU/g, cellobiase units per gram dry material. Ethanol content is shown at fermentation time 0 h and time 48 h.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in fermentation, biofuels production, agricultural food, feed, and nutrition, or related fields are intended to be within the scope of the following claims.

What is claimed is:

1. A composition for generation of ethanol from a lignocellulosic feedstock comprising a lignocellulosic feedstock degradation composition, wherein the lignocellulosic feedstock degradation composition comprises:
   a) a lignocellulosic priming feedstock; wherein the lignocellulosic priming feedstock comprises dried distiller's grains (DDG) or dried distiller's grains with solubles (DDGS); and
   b) one or more lignocellulose-degrading microbes, wherein the one or more lignocellulose-degrading microbes are selected from the group consisting of *Aspergillus niger, Aspergillus oryzae*, and *Rhizopus oligosporus;*
   wherein the lignocellulose feedstock degradation composition is generated via incubation of the lignocellulosic priming feedstock with the one or more lignocellulose-degrading microbes under solid state fermentation conditions; and
   wherein the lignocellulosic feedstock degradation composition, when added to an ethanologenic fermentation of lignocellulosic feedstock, increases the yield of ethanol obtained from the ethanologenic fermentation by at least 9% compared to the yield of ethanol from ethnologenic fermentation of the lignocellulosic feedstock in the absence of the lignocellulosic feedstock degradation composition.

2. The composition of claim 1, wherein the *Rhizopus oligosporus* is *Rhizopus oligosporus* strain 2UV3.

3. The composition of claim 1, wherein said lignocellulosic feedstock is selected from the group consisting of forest residue, mill waste, urban wood waste, agricultural residues, bioenergy crops, stover, quinoa, corn husks, corn cobs, corn fiber, wheat straw, milo stubble, switchgrass, deciduous wood, coniferous wood, deciduous or coniferous wood chips, deciduous or coniferous sawdust, citrus waste, urban green waste or residue, food manufacturing industry waste or residue, cereal manufacturing waste or residue, hay, straw, rice straw, sugarcane, sugarcane bagasse, grain cleanings, spent brewer's grain, rice hulls, barley straw, salix, spruce, poplar, eucalyptus, *Brassica carinata* residue, *Antigonum leptopus*, sweetgum, *Miscanthus, Sericea lespedeza*, Chinese tallow, hemp, rapeseed, *Sorghum bicolor*, soybean leaves, soybeans stems, soybean pods, soybean residue, sunflower leaves, sunflower stems, seedless sunflower heads, sunflower hulls, sunflower residue, Arundo, nut shells, deciduous leaves, cotton fiber, manure, coastal Bermuda grass, clover, Johnsongrass, flax, buckwheat straw, oat straw, millet straw, amaranth straw, amaranth stems, amaranth leaves, amaranth residue, spelt straw, rye straw, alfalfa, and bamboo.

4. The composition of claim 3, wherein said spent brewer's grain is dried distiller's grain (DDG) or dried distiller's grain with solubles (DDGS).

5. The composition of claim 1, wherein solid state fermentation of the lignocellulosic priming feedstock with the one or more lignocellulose-degrading microbes comprises incubating the lignocellulosic priming feedstock and the one or more lignocellulose-degrading microbes at 20-40° C. for at least 5 days.

6. A method of producing ethanol from an ethanologenic feedstock comprising:
   1) providing:
      a) a lignocellulosic feedstock degradation composition comprising a lignocellulosic priming feedstock; wherein the lignocellulosic priming feedstock comprises dried distiller's grains (DDG) or dried distiller's grains with solubles (DDGS); and one or more lignocellulosic-degrading microbes, wherein the one or more lignocellulosic-degrading microbes are selected from the group consisting of *Aspergillus niger, Aspergillus oryzae*, and *Rhizopus oligosporus*; wherein the lignocellulosic feedstock degradation composition is generated via incubation of the lignocellulosic priming feedstock with the one or more lignocellulosic-degrading microbes under solid state fermentation conditions; and wherein the lignocellulosic feedstock degradation composition, when added to an ethanologenic fermentation of lignocellulosic feedstock, increases the yield of ethanol obtained from the ethanologenic fermentation by at least 9% compared to the yield of ethanol from ethanologenic fermentation of the lignocellulosic feedstock in the absence of the lignocellulosic feedstock degradation composition; and b) an ethanologenic feedstock comprising a lignocellulosic component; and 2) incubating the ethanologenic feed stock with the lignocellulosic feedstock degradation composition.

7. The method of claim 6, wherein the ethanologenic feedstock is comprised of a feedstock selected from the group consisting of grains, storage roots, tubers, nuts, fruits, corn (maize), wheat, rice, oats, barley, rye, amaranth, buckwheat, or spelt; potato, sweet potato, taro, yam, cassava, tapioca, arrowroot, cassava, legumes, chestnut, arracacha, banana, kudzu, oca, sago, and sorghum.

8. The method of claim 7, wherein said corn is in the form of corncobs or corn kernels.

9. A method for the production of ethanol from lignocellulosic feedstock, comprising:

i. providing a lignocellulosic feedstock degradation composition comprising a lignocellulosic priming feedstock; wherein the lignocellulosic priming feedstock comprises dried distiller's grains (DDG) or dried distiller's grains with solubles (DDGS); and one or more lignocellulosic-degrading microbes, wherein the one or more lignocellulosic-degrading microbes are selected from the group consisting of *Aspergillus niger, Aspergillus oryzae*, and *Rhizopus oligosporus*; wherein the lignocellulosic feedstock degradation composition is generated via incubation of the lignocellulosic priming feedstock with the one or more lignocellulosic-degrading microbes under solid state fermentation conditions; and wherein the lignocellulosic feedstock degradation composition, when added to an ethanologenic fermentation of lignocellulosic feedstock, increases the yield of ethanol obtained from the ethanologenic fermentation by at least 9% compared to the yield of ethanol from ethanologenic fermentation of the lignocellulosic feedstock in the absence of the lignocellulosic feedstock degradation composition;

ii. providing an ethanologenic feedstock capable of utilization as substrate by an ethanologenic microbe in a saccharification step;

iii. mixing the lignocellulosic feedstock degradation composition with the ethanologic feedstock under conditions sufficient to promote saccharification of the ethanologenic feedstock; and iv. conducting ethanologenic fermentation on the ethanologenic feedstock.

10. The method of claim 9, wherein the ethanologenic feedstock is comprised of one or more starch-rich feedstock selected from among the group consisting of grains, storage roots, tubers, nuts, fruits, corn (maize), wheat, rice, oats, barley, rye, amaranth, buckwheat, or spelt; potato, sweet potato, taro, yam, cassava, tapioca, arrowroot, cassava, legumes, chestnut, arracacha, banana, kudzu, oca, sago, and sorghum.

11. The composition of claim 1, wherein the lignocelluloseic feedstock degradation composition, when added to an ethanologenic fermentation of lignocellulosic feedstock, increases the yield of ethanol obtained from the ethanologenic fermentation by at least 20% compared to the yield of ethanol from ethnologenic fermentation of the lignocellulosic feedstock in the absence of the lignocellulosic feedstock degradation composition.

* * * * *